US010353376B2

(12) United States Patent
Huang et al.

(10) Patent No.: US 10,353,376 B2
(45) Date of Patent: Jul. 16, 2019

(54) SYSTEMS AND METHODS FOR MODELLING ADDITIVELY MANUFACTURED BODIES

(71) Applicant: ALCOA INC., Pittsburgh, PA (US)

(72) Inventors: Wei Huang, Monroeville, PA (US); Michael A. Globig, New Kensington, PA (US); John Siemon, Cheswick, PA (US); Robert J. Speer, Upper Burrell, PA (US)

(73) Assignee: ARCONIC INC., Pittsburgh, PA (US)

( * ) Notice: Subject to any disclaimer, the term of this patent is extended or adjusted under 35 U.S.C. 154(b) by 444 days.

(21) Appl. No.: 15/011,184

(22) Filed: Jan. 29, 2016

(65) Prior Publication Data

US 2016/0224017 A1 Aug. 4, 2016

Related U.S. Application Data

(60) Provisional application No. 62/109,411, filed on Jan. 29, 2015.

(51) Int. Cl.
*G06F 19/00* (2018.01)
*G05B 19/4099* (2006.01)
(Continued)

(52) U.S. Cl.
CPC ........ *G05B 19/4099* (2013.01); *B22F 3/1055* (2013.01); *B29C 64/153* (2017.08); *B29C 64/386* (2017.08); *B33Y 10/00* (2014.12); *B33Y 50/02* (2014.12); *G01N 21/9515* (2013.01); *G06T 7/0004* (2013.01); *B22F 2003/1057* (2013.01); *G05B 2219/49023* (2013.01); *G06K 2209/19* (2013.01);
(Continued)

(58) Field of Classification Search
CPC .... G05B 19/4099; B33Y 10/00; B33Y 50/02; B33Y 80/00; B33Y 40/00; G01N 21/9515; B29C 64/153; B29C 64/386
See application file for complete search history.

(56) References Cited

U.S. PATENT DOCUMENTS 5,517,420 A 5/1996 Kinsman et al.
7,043,330 B2 5/2006 Toyserkani et al.
(Continued)

OTHER PUBLICATIONS

Bamberg J., et al., "In-process control of selective laser melting by quantitative optical tomography", 19th World Conference on Non-Destructive Testing, 2016.
(Continued)

*Primary Examiner* — Alonzo Chambliss
(74) *Attorney, Agent, or Firm* — Greenberg Traurig, LLP

(57) ABSTRACT

Methods for creating three-dimensional volume quality models of additively manufactured metal bodies are disclosed. In one embodiment, a method comprises additively manufacturing each metal layer of a metal body. One or more images of the first metal layer are obtained. The image(s) are processed to detect and map potential manufacturing defects in the first metal layer. A two-dimensional contour of the first metal layer is generated from the three-dimensional CAD model. The mapped defects are integrated into the two-dimensional contour. A first layer of a three-dimensional volume quality model of the metal body is created based on the integrated two-dimensional contour.

20 Claims, 33 Drawing Sheets

(51) Int. Cl.

| | |
|---|---|
| *B22F 3/105* | (2006.01) |
| *G01N 21/95* | (2006.01) |
| *G06T 7/00* | (2017.01) |
| *B33Y 10/00* | (2015.01) |
| *B33Y 50/02* | (2015.01) |
| *B29C 64/153* | (2017.01) |
| *B29C 64/386* | (2017.01) |

(52) U.S. Cl.
CPC .............. *G06T 2207/10016* (2013.01); *G06T 2207/10048* (2013.01); *G06T 2207/30136* (2013.01); *Y02P 10/295* (2015.11); *Y02P 80/40* (2015.11)

(56) References Cited

U.S. PATENT DOCUMENTS

| | | | |
|---|---|---|---|
| 8,666,142 | B2 | 3/2014 | Shkolnik et al. |
| 2009/0206065 | A1 | 8/2009 | Kruth et al. |
| 2014/0163717 | A1 | 6/2014 | Das et al. |
| 2014/0308153 | A1 | 10/2014 | Ljungblad |
| 2015/0177158 | A1* | 6/2015 | Cheverton ......... G01N 15/0227 700/119 |
| 2015/0261196 | A1* | 9/2015 | Wilson ................ B33Y 10/00 700/119 |
| 2016/0182048 | A1* | 6/2016 | Shin ............... H03K 19/017509 345/213 |
| 2018/0169948 | A1 | 6/2018 | Coeck et al. |
| 2018/0178449 | A1 | 6/2018 | Cheverton et al. |

OTHER PUBLICATIONS

Clijsters, S. et al., "In situ quality control of the selective laser process using a high-speed, real-time melt pool monitoring system", *International Journal of Advanced Manufacturing Technology* 75(5-8):1089-1101, Aug. 10, 2014.

Craeghs, T, et al., "Online quality control of selective laser melting", Katholieke Universiteit Leuven, Heverlee, Belgium, pp. 212-226, 2011.

Craeghs, T, et al., "Feedback control of layerwise laser melting using optical sensors", *Physics Procedia* 5:505-514, 2010.

Hu, D. et al., "Sensing, modeling and control for laser-based additive manufacturing" *International Journal of Machine Tools & Manufacture* 43:51-60, 2003.

Jacobsmuhlen, J. zur, et al. "High Resolution Imaging for Inspection of Laser Beam Melting Systems", pp. 1-29, Instrumentation and Measurement Technology Conference (I2MTC), 2013 IEEE International, Minneapolis, Minnesota.

Jeng, J.-Y. et al., "On-line layer profile dimensions measurement of model maker rapid prototyping using vision technology ", *International Journal of Advanced Manufacturing Technology* 17(2):125-133, 2001.

Kleszczynski, S., et al., Error Detection in Laser Beam Melting Systems by High Resolution Imaging, Proceedings of the $23^{rd}$ Annual International Solid Freeform Fabrication Symposium, Institute of Imaging & Computer Vision, Aachen, Germany, 2012.

Krauss, H., et al., "Thermography for monitoring the selective laser melting process", Proceedings of the Solid Freeform Fabrication Symposium, pp. 999-1014, Austin, Texas, 2012.

Mireles, J. et al., "Close-loop automatic feedback control in electron beam melting", *International Journal of Advanced Manufacturing Technology* 78(5):1193-1199, 2015.

Wen-Hsiang, Tsai., "Moment-preserving thresholding: a new approach", *Computer Vision, Graphics and Image Processing* 29(3):377-393, 1985.

Zalameda, J. N., et al., "Thermographic Imaging of the Space Shuttle During Re-Entry Using a Near Infrared Sensor", International Society for Optical Engineering, 2012 SPIE Thermosense; Apr. 23-27, 2012; Baltimore, MD; United States, Apr. 2012.

International Search Report and Written Opinion, dated May 2, 2016, from corresponding International Patent Application No. PCT/US2016/015777.

\* cited by examiner

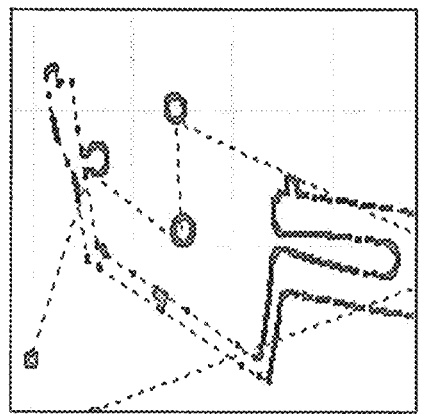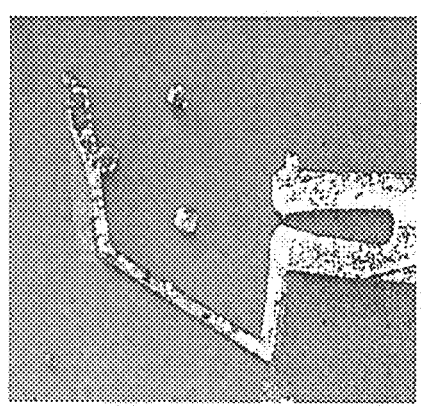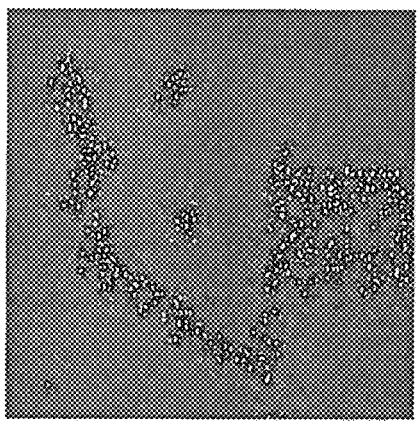

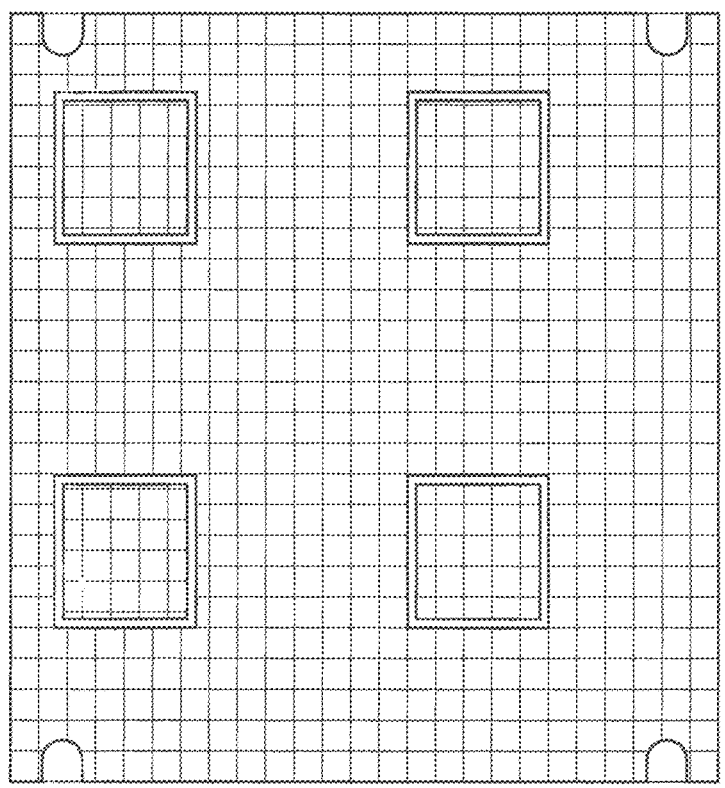

| ROW | HEIGHT | DIAMETER | | | | | | | | |
|---|---|---|---|---|---|---|---|---|---|---|
| | | 0.25 mm 0.63/64" | 0.5 mm 1.26/64" | 0.75 mm 1.89/64" | 1.00 mm 2.52/64" | 2.00 mm 5.04/64" | 3.00 mm 7.56/64" | 4.00 mm 10.08/64" | 6.00 mm 15.12/64" | 8.00 mm 20.16/64" |
| 1 | 0.09 mm (3 LAYERS) | | | | | | | | | |
| 2 | 0.15 mm (5 LAYERS) | | | | | | | | | |
| 3 | 0.3 mm (10 LAYERS) | | | | | | | | | |
| 4 | 0.75 mm (25 LAYERS) | | | | | | | | | |
| 5 | 1.5 mm (50 LAYERS) | | | | | | | | | |

LAYER # 112

LAYER # 120

SYSTEMS AND METHODS FOR MODELLING ADDITIVELY MANUFACTURED BODIES

CROSS-REFERENCE TO RELATED APPLICATIONS

This application is a non-provisional of and claims priority to U.S. Application Ser. No. 62/109,411, entitled "Methods for Creating Three-Dimensional Volume Quality Models of Additively Manufactured Metal Bodies" filed on Jan. 29, 2015, which is incorporated by reference in its entirety.

BACKGROUND

Additive manufacturing may be used to build, via computer control, successive layers of a metal body. Defects in the metal body may occur as a result of the additive manufacturing process.

FIELD Of THE INVENTION

Broadly, the present disclosure relates to systems and methods of creating three-dimensional volume quality models of additively manufactured metal bodies. More specifically, the present disclosure is directed towards systems and methods of utilizing images obtained during the AM build and processing those images to extract information indicative of defects detected on the AM part in situ during the build.

SUMMARY

Broadly, the present patent application relates to systems and methods of creating three-dimensional volume quality models of additively manufactured metal bodies. More specifically, the present disclosure is directed towards utilizing images obtained during the AM build and processing those images to extract information indicative of defects (e.g. drag, super elevation, and/or thermal events).

In some embodiments, events occurring throughout the AM build or during discrete times within a build can result in residual stress, heat conduction, and/or process parameters in the AM part that has distortion and/or shrinkage. Two non-limiting indicators of distortion and/or shrinkage during build (in situ during AM) include characteristics in the build part include: drag (e.g. non-uniform powder distribution) and super elevation (height above threshold build height). Two indicators of distortion and/or problems in building include non-uniform temperature and/or non-uniform part quality.

In some embodiments, systems and methods are provided for detecting and quantifying drag during an AM part build. In some embodiments, systems and methods are provided for detecting and mapping drag during an AM part build. In some embodiments, systems and methods are provided for detecting and quantifying super elevation that occurs during an AM part build. In some embodiments, systems and methods are provided for detecting and mapping super elevation during an AM part build. In some embodiments, systems and methods are provided for detecting and quantifying thermal events (peak temperature) during an AM part build. In some embodiments, systems and methods are provided for detecting and mapping thermal events (peak temperature) during an AM part build.

In some embodiments, systems and methods are provided for creating a three dimensional quality model for defects that occurs during an AM part build.

In some embodiments, systems and methods are provided for creating a three dimensional quality model for drag that occurs during an AM part build. In some embodiments, systems and methods are provided for creating a three dimensional quality model for super elevation that occurs during an AM part build. In some embodiments, systems and methods are provided for creating a three dimensional quality model for thermal events (defects) that occurs during an AM part build.

In some embodiments, systems and methods are provided for creating a three dimensional quality model for thermal events (defects) that occurs during an AM part build and comparing the model to NDE testing evaluation (CT, X-ray, and/or UT)

In some embodiments, systems and methods are provided for creating a three dimensional quality model configured to enable early detection of defects indicative of a "stop build" event during AM part production. In some embodiments, systems and methods are provided for creating a three dimensional quality model configured to enable early detection of defects and adjusting of AM process parameters in order to ameliorate/fix the defect during AM part production.

In one aspect, a method is provided, comprising: (A) obtaining a first digital image with a camera, where the first digital image is of at least a portion of a powder bed including a layer of metal powder distributed over a layer of additively manufactured body; wherein the first digital image has a plurality of pixels; wherein each pixel of the plurality of pixels has a specific intensity value; (B) translating by a processor the first digital image into a first binary image having non-drag particles: (C) filtering by the processor non-drag particles from the first binary image, (D) identifying by the processor all remaining particles in the first binary image as drag particles associated with the spreading of the layer of metal powder step (A); (E) mapping by the processor the drag associated with the spreading of the layer of metal powder step (A), wherein the mapping comprises a mapping a series of coordinates (e.g. x, y, z location) of location, size, and type of each respective drag particle for the layer of metal powder; (f) registering the map in a list form; (g) repeating (a)-(f) for a successive number of layers to create a defects registration list including the list for each layer; (h) converting by the processor the 3D CAD model to 2D contour for each layer; (i) extracting by the processor the coordinates of detected defects from the registration list for a single layer and embed/map into the corresponding 2D contour for that layer; (j) repeating g&h for all layers to yield a three dimensional volume quality model of the metal body including all the detected defects at each layer.

In one aspect, a method is provided, comprising: (A) obtaining a first digital image of at least a portion of a powder bed including a layer of metal powder distributed over a layer of additively manufactured body; wherein the first digital image has a plurality of pixels; wherein each pixel of the plurality of pixels has a specific intensity value; (B) translating the first digital image into a first binary image having non-drag particles: (C) filtering non-drag particles from the first binary image: (D) identifying all remaining particles in the first binary image as drag particles associated with the spreading of the layer of metal powder step (A); (E) mapping the drag associated with the spreading of the layer of metal powder step (A), wherein the mapping comprises a location and size of each respective drag particle; (F) creating a first layer of a three dimensional volume quality model of the metal body based at least in part on the location and size of each drag particle associated with the spreading of the layer of metal powder step (A).

In one aspect, a method is provided, where the translating step further comprises: (i) determining a global average intensity value of the plurality of pixels; (ii) resetting any specific intensity value that exceeds a threshold value to be equal to the global average intensity value; (iii) determining a local average intensity value for each pixel of the plurality of pixels; (iv) subtracting the specific intensity value of each pixel of the plurality of pixels from the local average intensity value, thereby determining a background-corrected intensity value for each pixel of the plurality of pixels; (v) replacing the specific intensity value of each pixel with its determined background-corrected intensity value; and (vi) performing a thresholding operation on the digital image, thereby creating the first binary image; wherein the first binary image has a plurality of binary pixels; further wherein the plurality of binary pixels comprises a plurality of particles.

In one aspect, the filtering step further comprises: (i) performing an x-axis close operation on each binary pixel of the plurality of binary pixels; (ii) removing from the first binary image all particles having a particle width below a threshold width; (iii) removing from the first binary image all particles having a particle elongation ratio below a threshold ratio; (iv) performing a dilation operation on the first binary image; (v) determining the number of on-pixels in each row of the first binary image; (vi) determining the number of particles in each row of the first binary image; and (vii) switching any on-pixels to off-pixels for any pixels in a row of the first binary image where the row has either a number of on-pixels less than a threshold on-pixel number, or a number of particles greater than a threshold particle number.

In one aspect, the mapping step comprises: (i) determining a location of each drag particle in the first binary image, (ii) determining a size of each drag particle, wherein a total number of pixels comprising each drag particle is representative of the size of each respective drag particle; and (iii) mapping the location and size of each drag particle to a respective location in the powder bed.

In one aspect, a method is provided, including: (A) utilizing a camera to obtain a first digital image of at least a portion of a powder bed including a layer of metal powder distributed over a layer of additively manufactured body and a portion of solidified molten metal indicative of an additive manufactured portion; wherein the first digital image has a plurality of pixels; wherein each pixel of the plurality of pixels has a specific intensity value; (B) first translating with a processor the first digital image into a first primary binary image via a moment-preserving thresholding operation; wherein the first primary binary image has a first plurality of particles comprising on-pixels; (C) second translating with the processor the first digital image into a first alternate binary image via a predetermined thresholding operation; wherein the first alternate binary image has a second plurality of particles comprising on-pixels; (D) filtering with the processor at least some non-super-elevation particles from the first alternate binary image, wherein the filtering comprises: (i) removing from the first alternate binary image all particles having a number of on-pixels less than a threshold number of on-pixels, thereby creating a first filtered binary image; (E) multiplying the first primary binary image with the first filtered binary image, thereby creating a first multiplied binary image; wherein the first multiplied binary image has a third plurality of particles comprising on-pixels; (F) identifying the third plurality of particles as super-elevation particles associated with the additively manufactured portion in step (A); (G) mapping the super-elevation, wherein the mapping comprises:
(i) determining a location of each super-elevation particle in the first multiplied binary image; (ii) determining a size of each super-elevation particle in the first multiplied binary image, wherein a total number of pixels comprising each super-elevation particle is representative of the size of that super-elevation particle; (iii) mapping the location and size of each super-elevation particle to a respective location in the metal body; and (H) creating a first layer of a three dimensional volume quality model of the metal body based at least in part on the mapping step.

In one aspect, a method is provided comprising: (A) using a camera to obtain a first sequential set of infrared images of the melt pool concomitant to additively manufacturing an AM body; wherein each infrared image comprises a plurality of pixels; wherein each pixel of the plurality of pixels has a specific intensity value; (B) correlating the specific intensity value of each pixel of each infrared image of the first sequential set to a temperature; (C) mapping the peak temperatures associated that from melt pool of step (A), wherein the mapping comprises: (i) determining a peak temperature point in each infrared image of the first sequential set; wherein each peak temperature point corresponds to the pixel representing the highest temperature in each respective infrared image; (ii) determining a location of each peak temperature point in its respective infrared image; (iii) mapping the location of each peak temperature point in its respective infrared image to a location on the first metal layer, thereby creating a first digital temperature map of the first metal layer; (D) creating a first layer of a three dimensional volume quality model of the metal body based on the mapping step (C).

In one embodiment, a method of creating a three-dimensional volume quality model of an additively manufactured metal body includes: spreading a first layer of metal powder on a powder bed, selectively melting (e.g. with a laser) at least a portion of the first layer of metal powder, thereby forming a melt pool comprising molten metal of the metal powder; solidifying the molten metal into a first metal layer of the metal body; and spreading a second layer of metal powder on the powder bed. The method may also include obtaining a first digital image of at least a portion of the powder bed, wherein the first digital image has a plurality of pixels, and wherein each pixel of the plurality of pixels has a specific intensity value.

The method may also include calibrating and correcting the first digital image, which may have perspective distortion due to the position and view angle of the digital camera, into a corrected digital image that the location of each image pixel is related to a respective location in the powder bed.

The method may also include translating the first digital image into a first binary image, wherein the translating comprises: determining a global average intensity value of the plurality of pixels; resetting any specific intensity value that exceeds a threshold value to be equal to the global average intensity value; determining a local average intensity value for each pixel of the plurality of pixels; subtracting the specific intensity value of each pixel of the plurality of pixels from the local average intensity value, thereby determining a background-corrected intensity value for each pixel of the plurality of pixels; replacing the specific intensity value of each pixel with its determined background-corrected intensity value; and performing a thresholding operation on the digital image, thereby creating the first binary image, wherein the first binary image has a plurality of binary pixels and, wherein the plurality of binary pixels comprises a plurality of particles. The method may include filtering non-drag particles from the first binary image, wherein the filtering comprises: performing an x-axis close operation on each binary pixel of the plurality of binary pixels; removing from the first binary image all particles having a particle width below a threshold width; removing from the first binary image all particles having a particle elongation ratio below a threshold ratio; performing a dilation operation on the first binary image; determining the number of on-pixels in each row of the first binary image; determining the number of particles in each row of the first binary image; switching any on-pixels to off-pixels for any pixels in a row of the first binary image where the row has either a number of on-pixels less than a threshold on-pixel number, or a number of particles greater than a threshold particle number; identifying all remaining particles in the first binary image as drag particles associated with the spreading a second layer step; and mapping the drag associated with the spreading a second layer step. The step of mapping the drag may comprise: determining a location of each drag particle in the first binary image; determining a size of each drag particle, wherein a total number of pixels comprising each drag particle is representative of the size of each respective drag particle; and mapping the location and size of each drag particle to a respective location in the powder bed. The method may include creating a first layer of a three dimensional volume quality model of the metal body based at least in part on the location and size of each drag particle associated with the spreading a second layer step.

In one embodiment, creating the first layer of the three dimensional volume quality model step comprises: generating a two dimensional contour of the first metal layer of the metal body from a pre-designed three-dimensional model of the metal body; integrating the location and size of each drag particle into the two dimensional contour of the first metal layer; and creating the first layer of the three dimensional volume quality model of the metal body based at least in part on the integrated contour of the first metal layer. In one embodiment, the two dimensional contour of the first metal layer may be extracted from a CLI (Common Layer Interface) file. In one embodiment, the pre-designed three-dimensional model of the metal body comprises an STL file. As used herein, STL means: a file format for 3D model data used by machines to build physical parts (e.g. where STL is the standard interface for AM systems).

In one embodiment, a method of creating a three-dimensional volume quality model of an additively manufactured metal body includes: selectively melting (e.g. with a laser) at least a portion of the second layer of metal powder, thereby forming a melt pool comprising molten metal of the metal powder; solidifying the molten metal into a second metal layer of the metal body; spreading a third layer of metal powder on the powder bed; obtaining a second digital image of at least a portion of the powder bed; translating the second digital image into a second binary image; filtering non-drag particles from the second binary image; identifying all remaining particles in the second binary image as drag particles associated with the spreading a third layer step; mapping the drag, thereby determining a location and size of each drag particle associated with the spreading a third layer step; and creating a second layer of the three dimensional volume quality model of the metal body based at least in part on the location and size of each drag particle associated with the spreading a third layer step. In one embodiment, the performing a thresholding operation step may comprise performing an interclass variance thresholding operation on the digital image.

In another aspect, a method of creating a three-dimensional volume quality model of an additively manufactured metal body includes: spreading a first layer of metal powder on a powder bed; selectively melting (e.g. with a laser) at least a portion of the first layer of metal powder, thereby forming a melt pool comprising molten metal of the metal powder; solidifying the molten metal into a first metal layer of a metal body; spreading a second layer of metal powder on the powder bed; obtaining a first digital image of at least a portion of the powder bed; translating the first digital image into a first primary binary image via a moment-preserving thresholding operation, wherein the first primary binary image has a first plurality of particles comprising on-pixels; second translating the first digital image into a first alternate binary image via a predetermined thresholding operation, wherein the first alternate binary image has a second plurality of particles comprising on-pixels; and filtering non-super-elevation particles from the first alternate binary image, wherein the filtering includes removing from the first alternate binary image all particles having a number of on-pixels less than a threshold number of on-pixels, thereby creating a first filtered binary image; multiplying the first primary binary image with the first filtered binary image, thereby creating a first multiplied binary image, wherein the first multiplied binary image has a third plurality of particles comprising on-pixels; identifying the third plurality of particles as super-elevation particles associated with the selectively melting step; and mapping the super-elevation. Mapping the super-elevation may include: determining a location of each super-elevation particle in the first multiplied binary image; determining a size of each super-elevation particle in the first multiplied binary image, wherein a total number of pixels comprising each super-elevation particle is representative of the size of that super-elevation particle; and mapping the location and size of each super-elevation particle to a respective location in the metal body. The method may include creating a first layer of a three dimensional volume quality model of the metal body based at least in part on the location and size of each super-elevation particle associated with the selectively melting step.

In one embodiment, the creating step includes: generating a two dimensional contour of the first metal layer of the metal body from a pre-designed three-dimensional model of the metal body; integrating the location and size of each super-elevation particle into the two dimensional contour of the first metal layer, and creating the first layer of the three dimensional volume quality model of the metal body based at least in part on the integrated contour of the first metal layer.

In one embodiment, the first translating step comprises performing a predetermined thresholding operation on the $n^{th}$ digital image. In one embodiment, the second translating step comprises performing a moment-preserving thresholding operation on the $n^{th}$ digital image.

In one embodiment, a method of creating a three-dimensional volume quality model of an additively manufactured metal body includes: selectively melting (e.g. with a laser) at least a portion of the second layer of metal powder, thereby forming a melt pool comprising molten metal of the metal powder; solidifying the molten metal into a second metal layer of the metal body; spreading a third layer of metal powder on the powder bed; obtaining a second digital image of at least a portion of the powder bed; translating the second digital image into a second primary binary image; second translating the second digital image into a second alternate binary image; filtering the second alternate binary image, thereby creating a filtered second alternate binary image; multiplying the second primary binary image with the filtered second alternate binary image, thereby creating a second multiplied binary image; identifying all particles of the second multiplied binary image as super-elevation particles associated with the selectively melting at least a portion of the second layer step; mapping the super-elevation, thereby determining a location and size of each super-elevation particle; and creating a second layer of the three dimensional volume quality model of the metal body based at least in part on the location and size of each super-elevation particle.

In another aspect, a method of creating a three-dimensional volume quality model of an additively manufactured metal body includes: spreading a first layer of metal powder on a powder bed; selectively melting at least a portion of the first layer of metal powder, thereby forming a melt pool comprising molten metal of the metal powder; solidifying the molten metal into a first metal layer of a metal body; concomitant to the selectively melting step (b), obtaining a first sequential set of infrared images of the melt pool, wherein each infrared image comprises a plurality of pixels, and wherein each pixel of the plurality of pixels has a specific intensity value; correlating the specific intensity value of each pixel of each infrared image of the first sequential set to a temperature; calibrating and correcting the sequential set of infrared images, which may have perspective distortion due to the position and view angle of the digital camera, into a corrected set of digital image that the location of each image pixel in each image is related to a respective location in the powder bed; mapping the peak temperatures associated with the selectively melting step. Mapping the peak temperatures may include: determining a peak temperature point in each infrared image of the first sequential set, wherein each peak temperature point corresponds to the pixel representing the highest temperature in each respective infrared image; determining a location of each peak temperature point in its respective infrared image; mapping the location of each peak temperature point in its respective infrared image to a location in the powder bed for the first metal layer, thereby creating a first digital temperature map of the first metal layer; and creating a first layer of a three dimensional volume quality model of the metal body based on the mapping step.

In one embodiment, the creating step includes: generating a two-dimensional contour of the first metal layer of the metal body from a pre-designed three-dimensional model of the metal body; integrating the location and size of each peak temperature point into the two dimensional contour of the first metal layer; and creating the first layer of the three dimensional volume quality model of the metal body based at least in part on the integrated contour of the first metal layer.

In one embodiment, a method of creating a three-dimensional volume quality model of an additively manufactured metal body includes: spreading a second layer of metal powder on a powder bed; selectively melting at least a portion of the second layer of metal powder, thereby forming a melt pool comprising molten metal of the metal powder; solidifying the molten metal into a second metal layer of a metal body; concomitant to the selectively melting step, obtaining a second sequential set of infrared images of the melt pool; correlating the specific intensity value of each pixel of each infrared image of the second sequential set to a temperature; and mapping the peak temperatures associated with the selectively melting at least a portion of the second layer step, wherein the mapping includes creating a first layer of a three dimensional volume quality model of the metal body based on the mapping step.

BRIEF DESCRIPTION OF THE DRAWINGS

FIG. 8b is a digital image of the nth metal layer of the metal bodies of FIG. 8a.

FIG. 9a is an illustration of a temperature map of the nth metal layer of a metal body.

FIG. 9b is a digital image of the nth metal layer of the metal body of FIG. 9a.

FIG. 9c is an illustration of a two-dimensional contour of the nth metal layer of the metal body of FIG. 9a.

FIG. 12 is a plan view of an embodiment of a calibration build pattern utilized in conjunction with a calibration method, in accordance with the instant disclosure. As depicted in FIG. 12, the build pattern consists of four squares in a spaced configuration from one another such that their sides are parallel. The plan view provides the build plate (substrate or base plate) with grid marks corresponding to x, y coordinates for the AM machine. The part design for calibration depicted in FIG. 12 includes four square frames built over a few hundred layers in an AM build. The parts (squares) are positioned and built inside of the building platform of the AM machine. The X and Y coordinates of the 4 corner points of the external edges of each square frame are pre-determined and known parameters, such that the X and Y coordinates of total 16 corner points are machine coordinates with respect to the building platform.

FIG. 13C and FIG. 13D are those same views, respectively, having been processed via a thresholding operation to depict only the part build in the image. FIG. 13A an example of a "first" captured visible image (original); FIG. 13B is an example of a "second" captured visible image (original) showing an additive manufacturing build progression on a build pattern used to calibrate the monitoring system components (cameras) in accordance with the instant disclosure. FIG. 13C is an example of the "first" threshold image of FIG. 13A, after a thresholding operation performed via a processor. FIG. 13D is an example of the "second" threshold image of FIG. 13B, after a thresholding operation is performed on the original image via a processor. The visible light camera has an exposure time of 1 second per image, which accumulates the visible light from the laser heating the powder and multiple layers are recorded to improve the coordinate system transformation accuracy.

FIG. 15C and FIG. 15D are those same views, respectively, having been processed via a thresholding operation to depict only the part build in the image. FIG. 15A an example of a "first" captured thermal image (original); FIG. 15B is an example of a "second" captured thermal image (original) showing an additive manufacturing build progression on a build pattern used to calibrate the monitoring system components (cameras) in accordance with the instant disclosure. FIG. 15C is an example of the "first" threshold image of FIG. 15A, after a thresholding operation performed via a processor. FIG. 15D is an example of the "second" threshold image of FIG. 15B, after a thresholding operation is performed on the original image via a processor. The camera for thermal imaging is exposed for 6 second per image (e.g. slightly longer than the 4-5 second build time for this AM part), which accumulates infrared light emitted by the laser heating the powder and multiple layers are again captured.

FIG. 17A depicts the edge detecting step providing the 'added visible image' of the calibration part build configured for obtaining the x, y coordinates of the calibration pattern build, with a plurality of lines in a grid pattern overlaid on the image in order to detect edge and corner points of the calibration part build. FIG. 17B is the calibrated visible image of FIG. 17A, showing the corrected visible image, created from a perspective transformation matrix (e.g. the mathematical model of the x, y coordinates of the calibration part from the perspective of the visible camera compared to and corrected by the machine coordinates (e.g. the plan view coordinates from the calibration part build depicted in FIG. 12).

FIG. 17C depicts the edge detecting step providing the 'added thermal image' of the calibration part build configured for obtaining the x, y coordinates of the calibration pattern build, with a plurality of lines in a grid pattern overlaid on the image in order to detect edges and extract corner points of the calibration part build (based on the detected edges). The X and Y image coordinates of all the 16 corner points are obtained, which are compared and calibrated to the machine coordinate system. A perspective transformation matrix is also obtained and saved, which is then used to remove perspective distortion. FIG. 17D is the calibrated visible image of FIG. 17C, showing the corrected thermal image, created from a perspective transformation matrix (e.g. the mathematical model of the x, y coordinates of the calibration part from the perspective of the thermal camera compared to and corrected by the machine coordinates (e.g. the plan view coordinates from the calibration part build depicted in FIG. 12). The new image has no perspective distortion and the visible image and thermal image share the same perspective of a plan-view of the part with a same machine coordinates. With this same perspective and same machine coordinates, the visible images and thermal images captured layer by layer can be integrated and used to reconstruct the three dimensional quality models in accordance with various embodiments described herein.

DETAILED DESCRIPTION

Reference will now be made in detail to the accompanying drawings, which at least assist in illustrating various pertinent embodiments of the new technology provided for by the present disclosure.

Figure 1A:
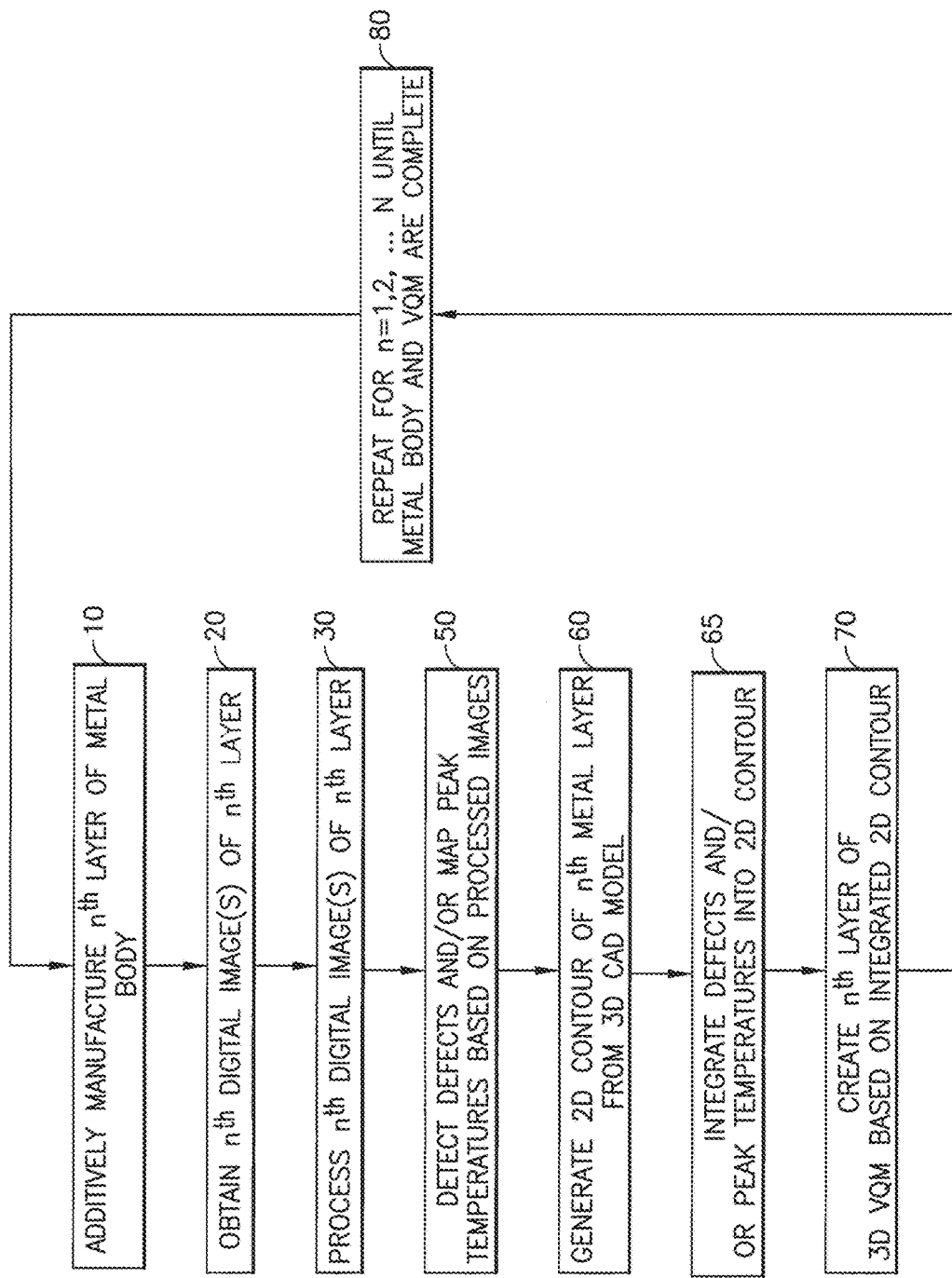
FIG. 1a is a schematic illustration of one embodiment of a method for creating three-dimensional volume quality models of additively manufactured metal bodies.

Referring now to FIG. 1a, one embodiment of a method for creating three-dimensional volume quality models of additively manufactured metal bodies is illustrated. In the illustrated method, metal bodies are additively manufactured layer by layer in a powder bed, according to a pre-designed three-dimensional CAD model. A first metal layer of a metal body is additively manufactured (10) according to the three-dimensional CAD model. One or more digital image(s) of the first metal layer and/or the powder bed are obtained (20) concomitant and/or subsequent to the additively manufacturing layer step (10). The digital image(s) are processed (30) to detect and map potential manufacturing defects, and generate the peak temperature map, in the first metal layer. A two-dimensional contour of the first metal layer is generated (60) from the three-dimensional CAD model. The mapped defects and generated peak temperature map are integrated (65) into the two-dimensional contour. A first layer of a three-dimensional volume quality model of the metal body is created (70) based on the two-dimensional contour with detected defects and detected peak temperature map (50). The above steps are repeated (80) for each successive metal layer (i.e., for layers n=1, 2, . . . N) until the metal body is built and the three-dimensional volume quality model (VQM) is complete.

Figure 1B:
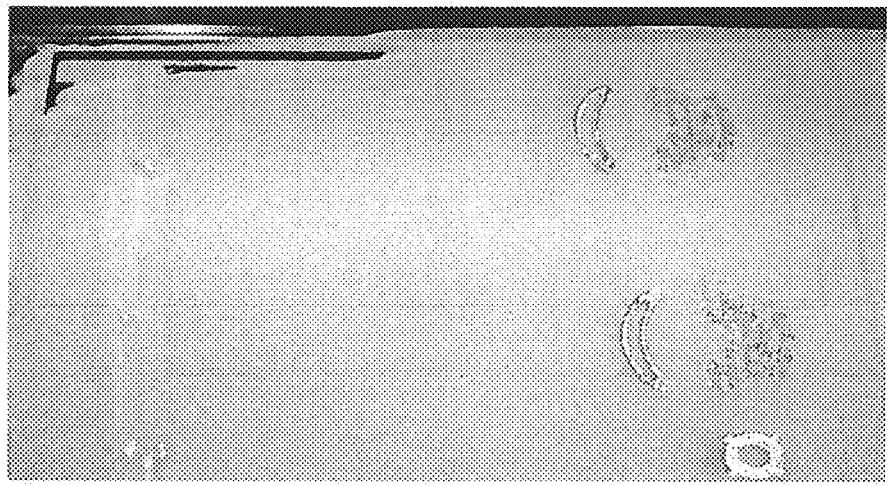
FIGS. 1b-d are examples of images of a powder bed.
Figure 1C:
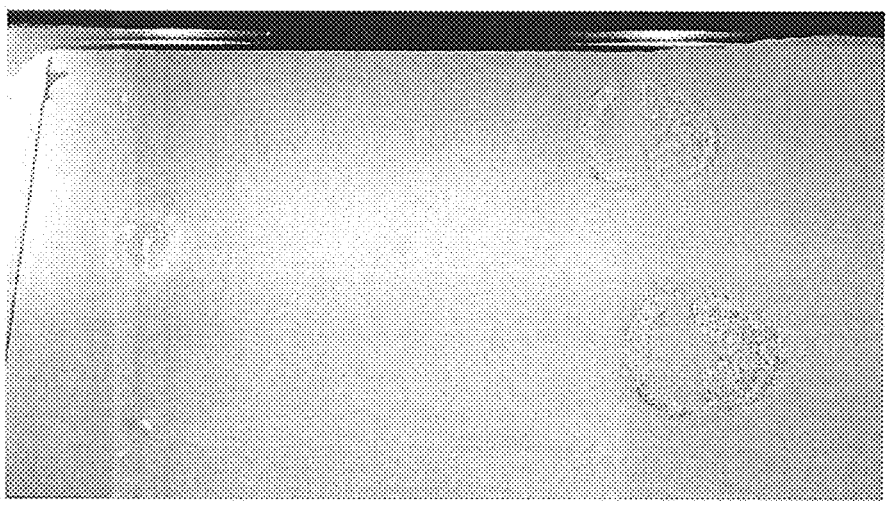
Figure 1D:
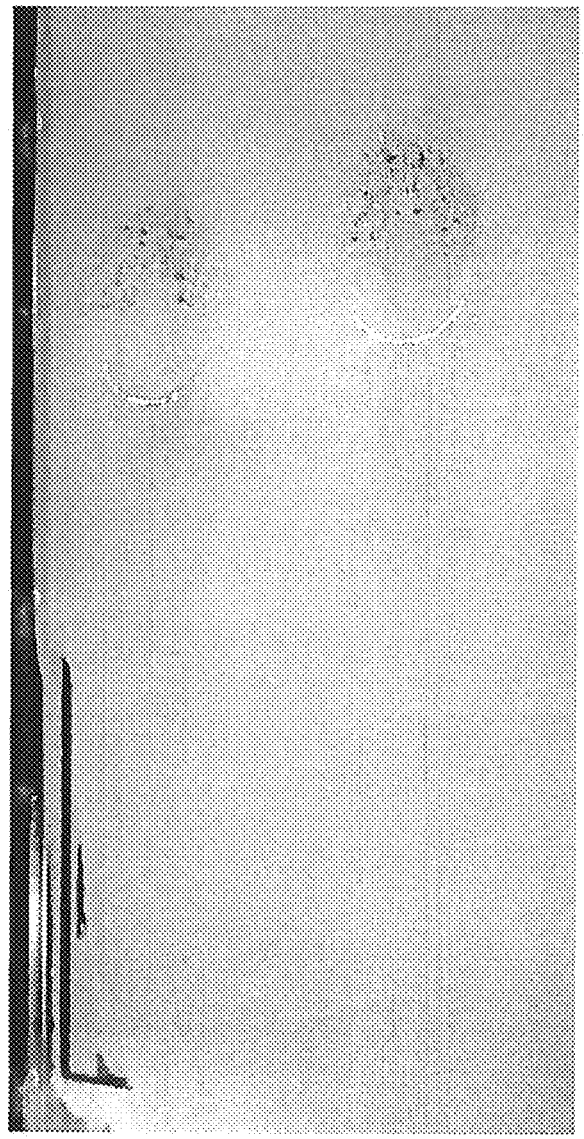

As mentioned above, one or more image(s) of the first metal layer and/or the powder bed are obtained (20) concomitant and/or subsequent to the additively manufacturing the layer step (10). In this regard, one or more images of a metal layer and/or powder bed may be obtained after a metal layer is built, but before the next layer of powder is spread over that metal layer. Similarly, one or one or more images of may be obtained after the next layer of powder is spread on top of the metal layer. FIG. 1b. is one embodiment of a digital image obtained after a metal layer is built, but before the next layer of powder is spread over that metal layer. FIG. 1c is one embodiment of a digital image obtained after a layer of powder is spread, from right to left as shown, over the metal layer and powder bed. As can be seen in the embodiment of FIG. 1c, the layer of powder is generally uniform and covers the metal layer completely. FIG. 1d is another embodiment of a digital image obtained after a layer of powder is spread, from right to left as shown, over the metal layer and powder bed. As can be seen in the embodiment of FIG. 1d, crescent-shaped portions of the metal layer protrude above the top of the layer of powder (i.e., super-elevation). Furthermore, horizontal patterns of non-uniform powder distribution (i.e., drag) can be seen to the left of the crescent-shaped super-elevation points.

In one embodiment, features such as defects, laser scan paths, dimensions, deviations, and/or temperatures may be combined to assess the quality of the metal body during or after a build. In one embodiment, the VQM may be examined in any desired plane and/or cross-section. In one embodiment, the VQM may be provided to an operator in real-time, allowing the operator to assess the additive manufacturing process as it progresses. In this regard, threshold defect values and associated alarms set may be set to alert the operator of problems in the additive manufacturing process. In another embodiment, threshold defect values may trigger an automatic termination of the additive manufacturing process. Thus, the VQM may allow rapid detection and diagnosis of problems with the additive manufacturing process, thereby saving time and materials.

As mentioned above, the three-dimensional volume quality model may include features such as defects in the metal body. These defects may include drag, super-elevation and/or non-uniform peak temperature distribution. As used herein, "drag" means a horizontal pattern of non-uniform powder distribution in a layer of powder due to distortion of the metal body. In one embodiment, drag may be caused by shrinkage of the metal body. Such shrinkage may be due to, for example, residual stress, or non-uniform heating of the metal body. In one embodiment, drag may be caused by super-elevation on the metal body. As used herein, "super-elevation" means a portion of a layer of an additively manufactured metal article wherein the portion extends above the intended height for that layer. In this regard, after a layer of powder is spread over the metal articles, super-elevation may protrude above the powder. As used herein, a "non-uniform peak temperature distribution" is a potential indication of defect due to a temperature deviation, for example, a high temperature deviation during a selectively melting step.

Figure 2A:
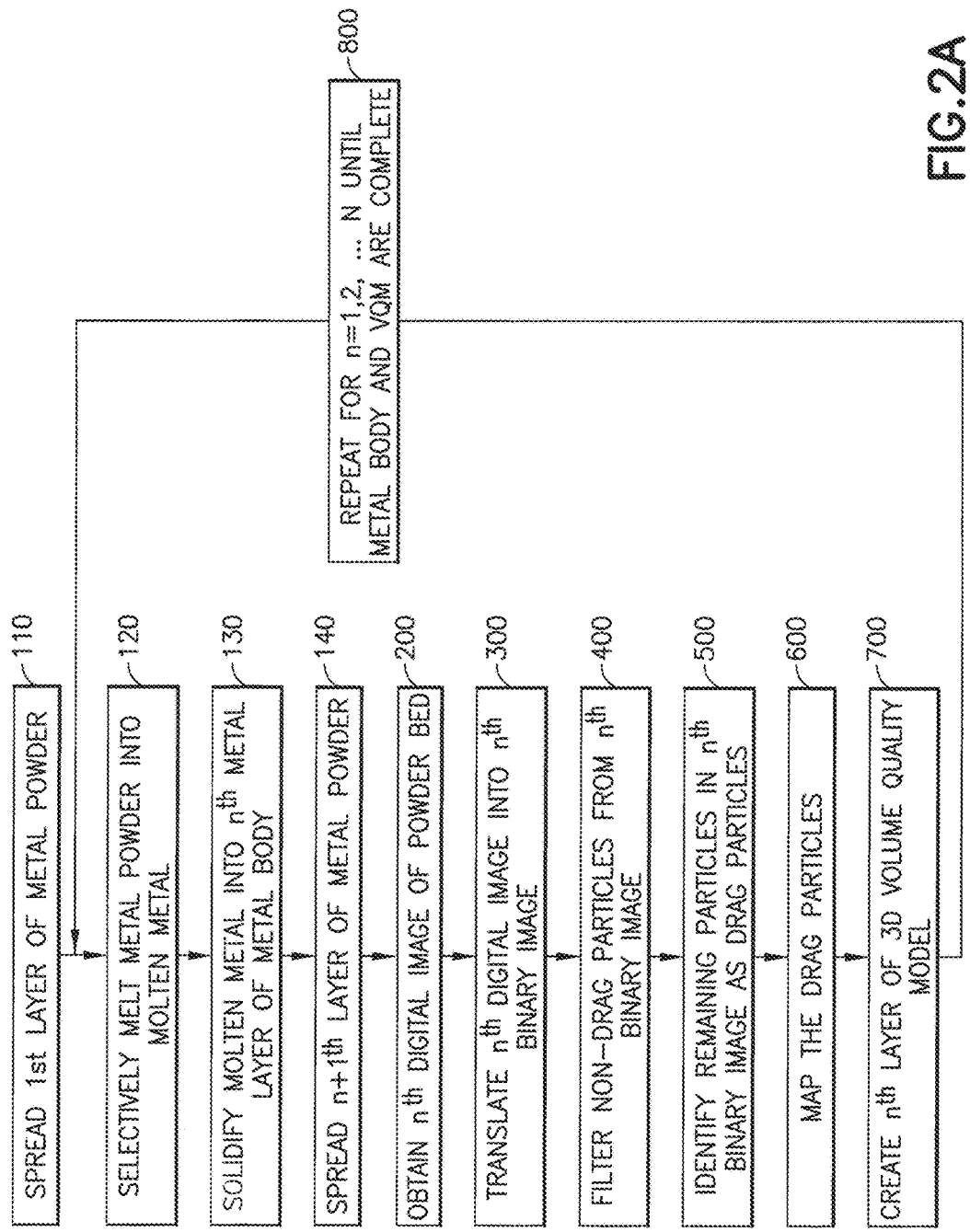
FIGS. 2a-c are schematic illustrations of one embodiment of a method for creating three-dimensional volume quality models based on detected drag defects in additively manufactured metal bodies.

Referring now to FIG. 2a, one embodiment of a method for creating three-dimensional volume quality models based on detected drag defects is illustrated. In the illustrated embodiment, a first metal layer of a metal body may be additively manufactured. In this regard, the first layer of metal powder may be spread (110) in the form of a powder bed (e.g. and/or on a build plate/substrate). At least a portion of the metal powder may be selectively melted (120), thereby forming a melt pool of molten metal. The molten metal may be solidified (130) into the nth (e.g., the first) layer of the metal body. In one embodiment, then, the nth+1 (e.g., the second) layer of metal powder may be spread (140) in the form of a powder bed, thereby covering the first metal layer of the metal body with powder.

As used herein, "additive manufacturing" and the like means a process of joining materials to make objects from 3D model data, usually layer upon layer. In some embodiments, additive manufacturing includes building successive layers of a metal powder (e.g., an aluminum alloy powder) by depositing a feed stock powder (metal powder) and then selectively melted and/or sintered (e.g. with a laser or other heat source) to create, layer-by-layer, an AM product (e.g., an metal product, an aluminum alloy product, a titanium alloy product, a nickel alloy product). Additive build processes utilizing a powder feedstock that can employ one or more of the embodiments of the instant disclosure include: direct metal laser sintering (e.g. a powder bed fusion process used to make metal parts directly from metal powders without intermediate "green" or "brown" parts); directed energy deposition (e.g. an AM process in which focused thermal energy is used to fuse materials by melting as they are being deposited); powder bed fusion (e.g. an AM process in which thermal energy selectively fuses regions of a powder bed); or laser sintering (e.g., a powder bed fusion process used to produce objects from powdered materials using one or more lasers to selective fuse or melt the particles at the surface, layer by layer, in an enclosed chamber) to name a few. Some non-limiting examples of suitable additive manufacturing systems include the EOSINT M 280 Direct Metal Laser Sintering (DMLS) additive manufacturing system, available from EOS GmbH (Robert-Stirling-Ring 1, 82152 Krailling/Munich, Germany). Other suitable additive manufacturing systems include Selective Laser Sintering (SLS) systems, Selective Laser Melting (SLM) systems, and Electron Beam Melting (EBM) systems, among others.

Figure 5A:
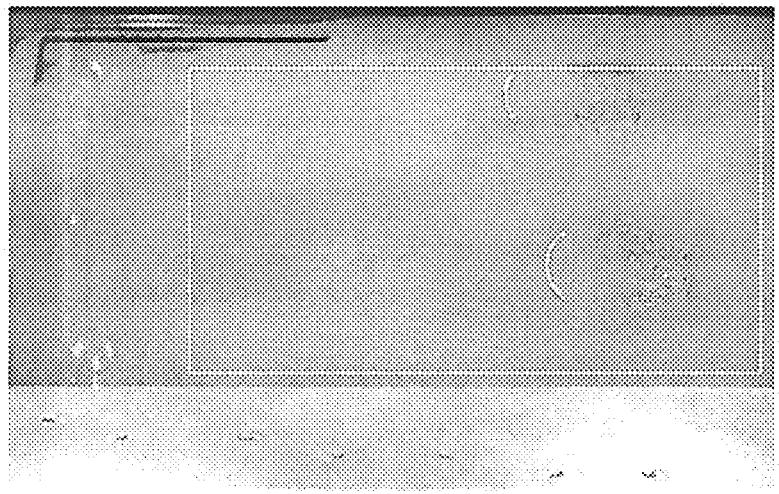
FIGS. 5a-d are examples of images produced in accordance with the disclosed methods.

As shown in FIG. 2a, the nth (e.g., a first) digital image of at least a portion of the powder bed may be obtained (200). One embodiment of a digital image of the powder bed and at least a portion of the build platform is shown in FIG. 5a. As used herein, a "digital image" is an image comprised of pixels. For example, pixels are the basic element of a digital image. Each pixel may have a specific intensity value associated with it. The specific intensity value of a pixel may indicate an electromagnetic characteristic (e.g., frequency of electromagnetic radiation, intensity of electromagnetic radiation, color, and/or appearance, among others) that is associated with that pixel. Intensity values may be limited to a discrete number of values. For example, for an 8 bit camera, the intensity values may be limited to all integers from 0 to 255 (i.e. 8 bit has intensity vales limited to all integers from 0~(28-1)). It is noted that any type of camera can be used (e.g. 16 bit camera has intensity values limited to all integers from 0~216-1).

Figure 5B:
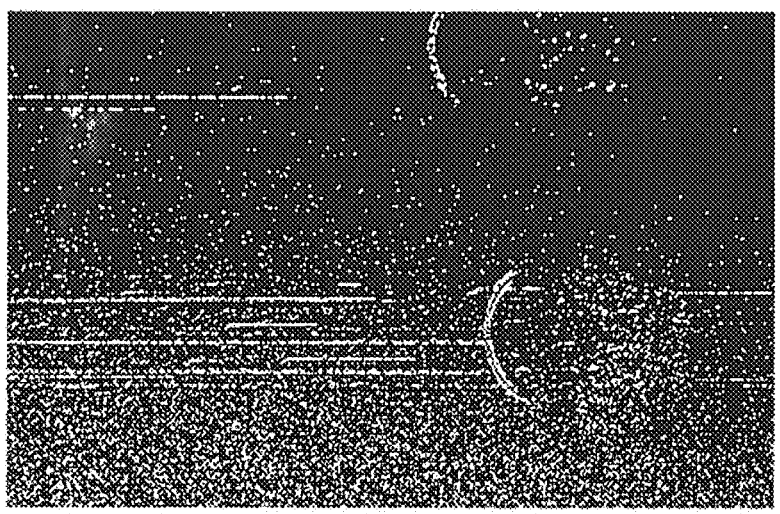

Turning back to FIG. 2a, the nth digital image may then be translated (300) into the nth binary image. As used herein, a "binary image" is a digital image comprised of binary pixels. As used herein "binary pixels" are pixels whose intensity values are limited to one of two possibilities. In one embodiment, binary pixels may be pixels whose intensity values are limited to the group consisting of 1 and 0. Binary pixels may be referred to as "on-pixels" and "off-pixels". An "on-pixel" is a pixel whose intensity value is 1, e.g., a white pixel. An "off-pixel" is a pixel whose intensity value is 0, e.g., a black pixel. FIG. 5b is one example of a binary image produced by translating (300) the digital image of FIG. 5a. The illustrated binary image includes particles, some of which depict defects such as drag or super-elevation and some which are a result of white noise in the digital image. As used herein, a "particle" is a group of contiguous on-pixels in a binary image.

Turning back to FIG. 2a, at least some of the non-drag particles (e.g., particles that depict super-elevation or are a result of white noise in the digital image) may be filtered (400) from the nth binary image.

Figure 5C:

The remaining particles in the nth binary image after the filtering step (400) may be identified (500) as drag particles. FIG. 5c is one example of a filtered binary image in which the particles have been identified (500) as drag particles. These identified drag particles may be associated with the additive manufacturing step of spreading (140) the nth+1 layer of metal powder on the powder bed.

The identified drag particles in the nth binary image may be mapped (600). The mapping step (600) may include determining a location of each drag particle in the first binary image. In one embodiment, the location of a drag particle may be determined via the coordinates of the pixels that make up the particle. The mapping step (600) may include determining the size of each drag particle. The size of a drag particle may be measured via the total number of pixels that make up the drag particle. The mapping step (600) may include correlating the location and/or size of each drag particle to a respective location in the powder bed. In one embodiment, the coordinates of the drag particle in the binary image may be used in conjunction with one or more landmarks in the image, such as the building platform, in order to map the drag particle to a location in the powder bed and/or metal body. Thus, x, y spatial coordinates of the drag particle (e.g., relative to the building platform) may be determined. The z coordinate of the drag particle in the powder bed may be determined, for example, via the layer number of the powder layer and/or metal layer and knowledge of a pre-determined layer thickness.

An nth layer of a three-dimensional volume quality model may then be created (700) based at least in part on the mapped drag particles. In one embodiment, a two-dimensional contour of the nth metal layer of the metal body may be generated from a pre-designed three dimensional CAD (computer-aided design) model. Then, the location and/or size of each drag particle may be integrated into the two-dimensional contour. An nth layer of the three-dimensional volume quality model may then be created based at least in part on the integrated two-dimensional contour.

The above steps (120 through 700) may be repeated (800) until the metal body and its corresponding three-dimensional volume quality model are complete. In one embodiment, the three-dimensional volume quality model is created concomitantly with the metal body. In this regard, as the layers of the metal body are completed, corresponding layers of the three-dimensional volume quality model may be created. In another embodiment, the creation of the three-dimensional volume quality model is not begun until after the metal body is complete. In this regard, the digital images of each layer of the metal body may be obtained and digitally stored to be processed at a later time.

Figure 6:
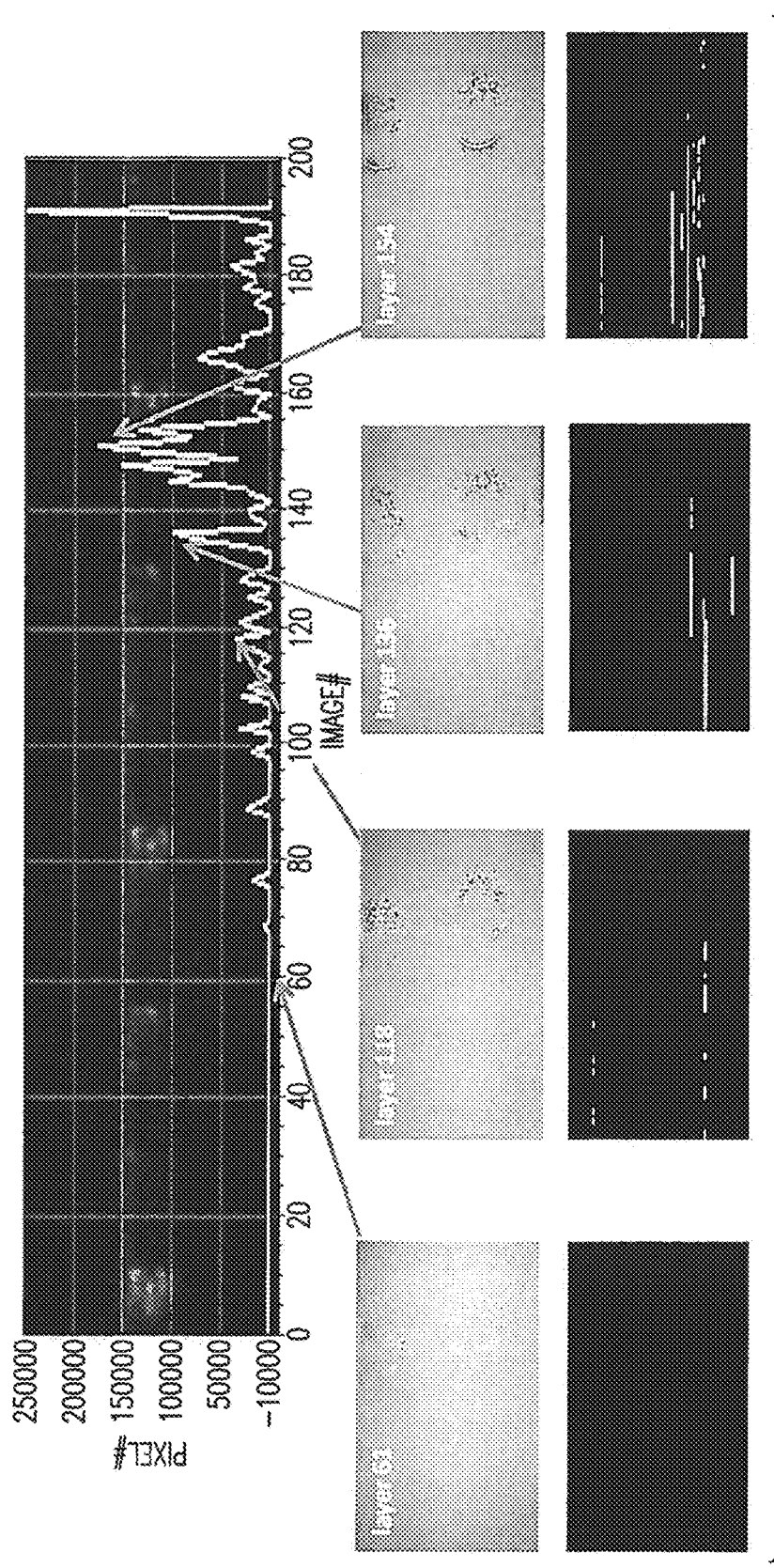
FIG. 6 is an example of a time-series chart showing the amount of drag detected in each layer of metal powder used to form a metal body.

Turning now to FIG. 6, as an alternative or in addition to a three dimensional VQM of the drag, a time-series chart of the drag particles detected at each layer of metal powder (i.e., for layers n=1, 2, . . . N) may be created. Specifically, a total number of on-pixels may be determined for the identified (500) drag particles detected at each layer of powder. Thus, the total number of on-pixels comprising the drag particles of each filtered binary image may represent the total amount of drag detected at the respective layer of metal powder.

Figure 2B:
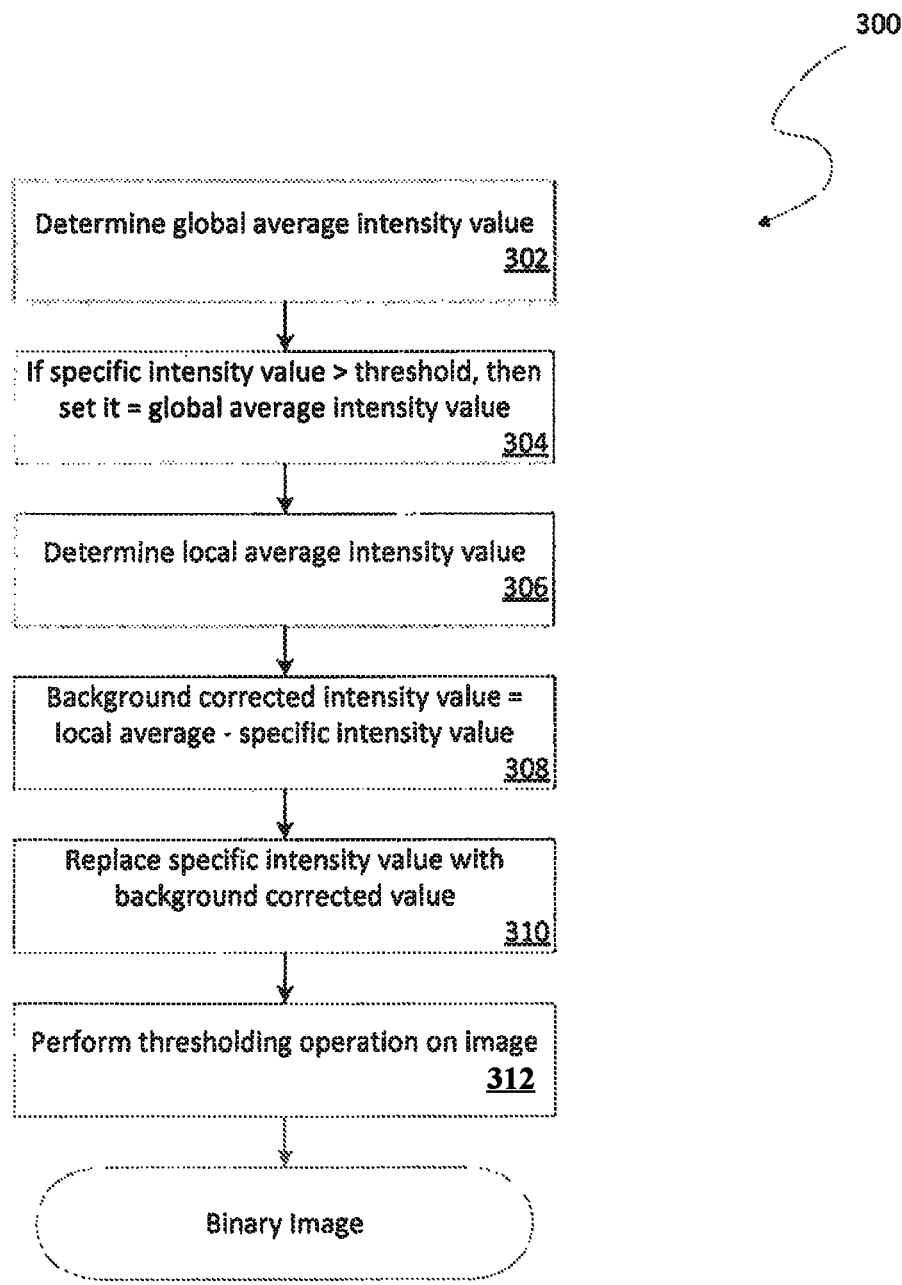

Referring now to FIG. 2b, one embodiment of translating (300) a digital image into a binary image is illustrated. In the illustrated embodiment, the translating step (300) includes sub-steps (302-312). First, a global average intensity value of the pixels in the digital image is determined (302). As used herein, a "global average intensity value" means the average intensity value of all of the pixels of a digital image. Next, the specific intensity value of each pixel is compared to a global threshold value (e.g., 100). If the specific intensity of a pixel does not exceed the threshold value, the next pixel is compared. If the specific intensity of a pixel exceeds the threshold value, then that specific intensity value is replaced (304) with the global average intensity value. Next, a local average intensity value may be determined (306) for each pixel. As used herein, a "local average intensity value" means the average intensity value of a portion of the pixels of a digital image. For example, a local average intensity value may be the average intensity value of the pixels with a 10 by 60rectangle of pixels. Then, a background-corrected intensity value is determined for each pixel by subtracting (308) its specific intensity value from its local average intensity value. Next, the specific intensity value of each pixel is replaced (310) with its background-corrected intensity value. Then, a thresholding operation is performed (314) on the digital image, thereby creating a binary image. As used herein, a "thresholding operation" means converting a digital image to a binary image based on each pixel's intensity value relative to other pixels in the image. In one embodiment, the thresholding operation is an interclass variance thresholding operation (i.e., "Otsu's method").

Figure 2C:
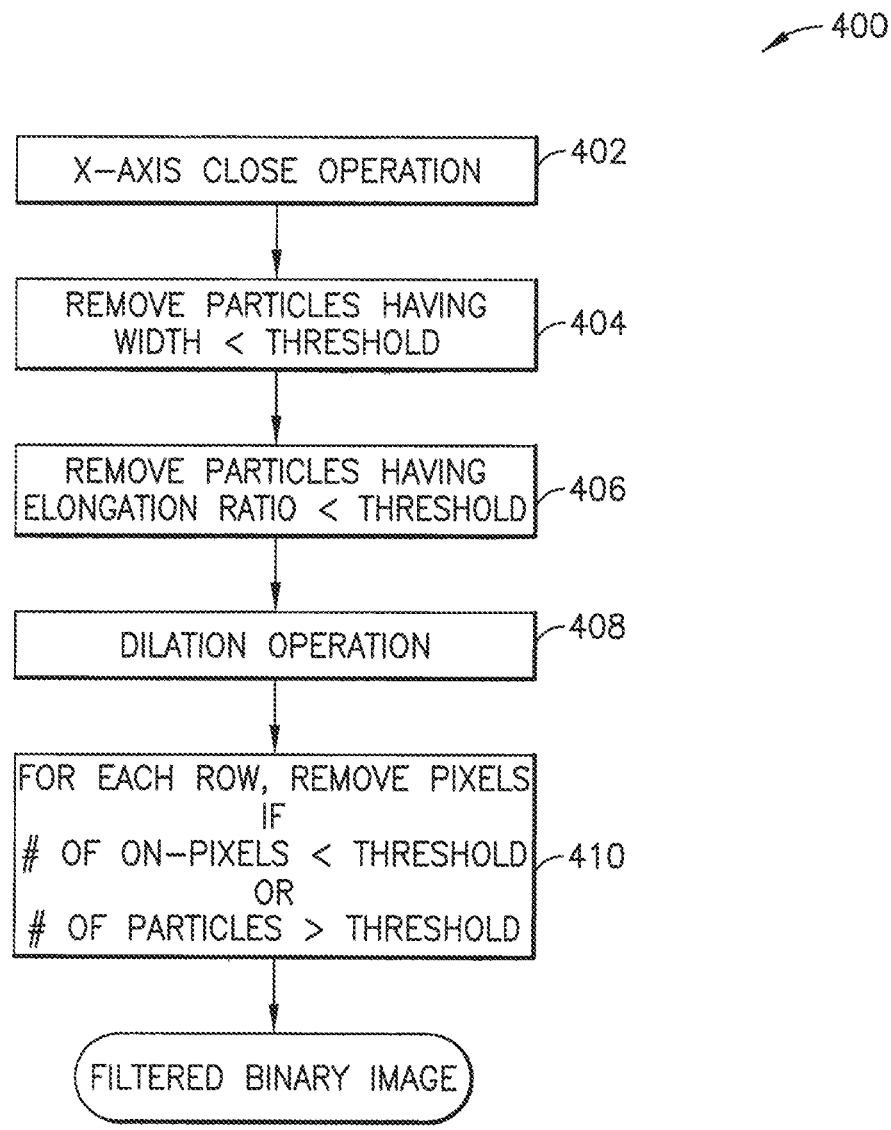

Referring now to FIG. 2c, one embodiment of filtering (400) non-drag particles from the binary image is illustrated. In the illustrated embodiment, the filtering step (400) includes sub-steps (402-414). First, an x-axis close operation may be performed (402) on the binary image. As used herein, an "x-axis close operation" means a dilation operation in only the x-axis of a digital image followed by an erosion operation in only the x-axis of the digital image. As used herein, a "dilation operation" means expanding (i.e., switching off-pixels to on-pixels at the edges of) the particles in a binary image. A dilation operation may use a structuring element (e.g., a 4×4square of pixels) for expanding such particles. As used herein, an "erosion operation" means contracting (i.e., switching on-pixels to off-pixels at the edges of) the particles in a binary image. An erosion operation may use a structuring element for contracting such particles. All particles having a particle width below a threshold particle width (e.g., 75) may be removed (404) from the binary image. As used herein, "particle width" is the dimension of a particle, measured in pixels, along the x axis of the binary image. As used herein, "removing particles" means switching all on-pixels of the particle to off-pixels. All particles having an elongation ratio below a threshold elongation ratio (e.g., 6) may be removed (406) from the binary image. As used herein, "particle elongation ratio" is the width of the particle divided by the particle height of the particle. As used herein, "particle height" is the dimension of a particle along the y axis of a binary image. A dilation operation may be performed (408) on the binary image. Next, each row of pixels is evaluated (410) any on-pixels in a may be switched to off-pixels for a row if the row has either a number of on-pixels less than a threshold on-pixel number (e.g., 500), or a number of particles greater than a threshold particle number (e.g., 50), Thus, a filtered binary image may be produced.

Figure 3:
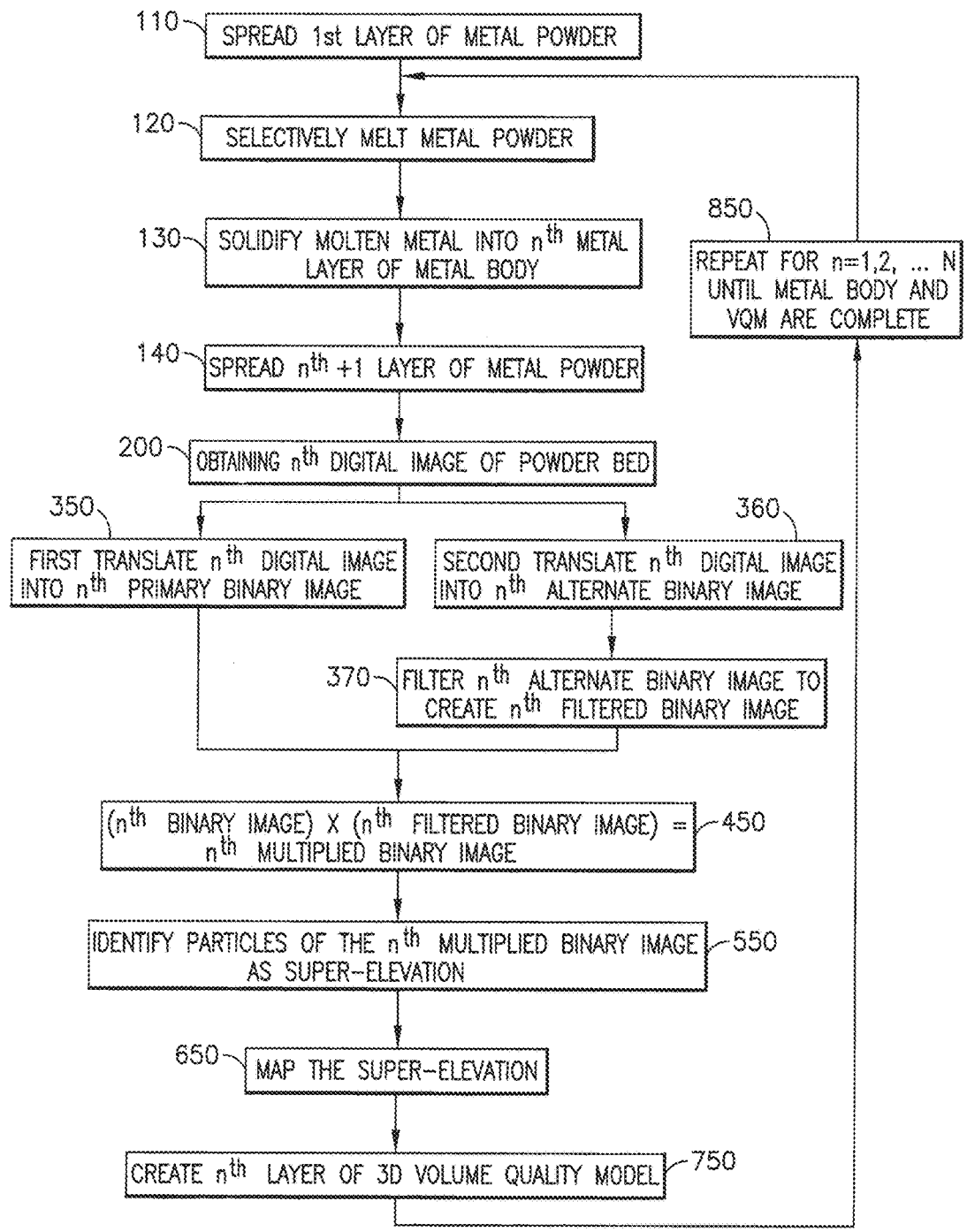
FIG. 3 is a schematic illustration of one embodiment of a method for creating three-dimensional volume quality models based on detected super-elevation defects in additively manufactured metal bodies.

Referring now to FIG. 3, one embodiment of a method for creating three-dimensional volume quality models based on detected super-elevation defects is illustrated. In the illustrated embodiment, a first metal layer of a metal body may be additively manufactured. In this regard, the first layer of metal powder may be spread (110) on the powder bed. At least a portion of the metal powder may be selectively melted (120), thereby forming a melt pool of molten metal. The molten metal may be solidified (130) into the nth (e.g., the first) layer of the metal body. Then, the nth+1 (e.g., the second) layer of metal powder may be spread (140) the on the powder bed, thereby covering the first metal layer of the metal body with powder.

As shown in FIG. 3, the nth (e.g., a first) digital image of at least a portion of the powder bed may be obtained (200). As discussed above, one embodiment of a digital image of the powder bed and at least a portion of the build platform is shown in FIG. 5a.

The nth digital image of the powder bed may be first translated (350) into an nth primary binary image. The nth digital image of the powder bed may be second translated (360) into an nth alternate binary image. The first and second translating steps (350, 360) may each comprise different thresholding operations. Thus, the nth primary binary image may be a different image than the nth alternate binary image. In one embodiment, the first translating step (350) comprises performing a predetermined thresholding operation on the nth digital image. In one embodiment, the second translating step (360) may comprise performing a moment-preserving thresholding operation on the nth digital image. As used herein, a "predetermined thresholding operation" means converting a digital image to a binary image based on a predetermined pixel intensity threshold. As used herein, a "moment-preserving thresholding" means converting a digital image to a binary image, wherein the average and the variance of the image intensity is preserved through the conversion process.

At least some of the non-super-elevation particles (e.g., particles that depict drag or are a result of white noise in the digital image) may be filtered (370) from the nth alternate binary image. The filtering step (370) may comprise removing from the nth alternate binary image all particles having a number of on-pixels less than a threshold number of on pixels (e.g., 200). Thus, an nth filtered binary image may be produced.

The nth primary binary image may be multiplied (450) with the nth filtered binary image, thereby creating an nth multiplied binary image. As used herein, "multiplying a first binary image with a second binary image" means multiplying the intensity value of each pixel in the first binary image with the intensity value of the pixel in the corresponding location in second binary image, thereby producing a third binary image. Thus, any on-pixel in the first binary image will be switched to an off-pixel in the third binary image unless the corresponding pixel in the second image is also an on-pixel.

Figure 5D:
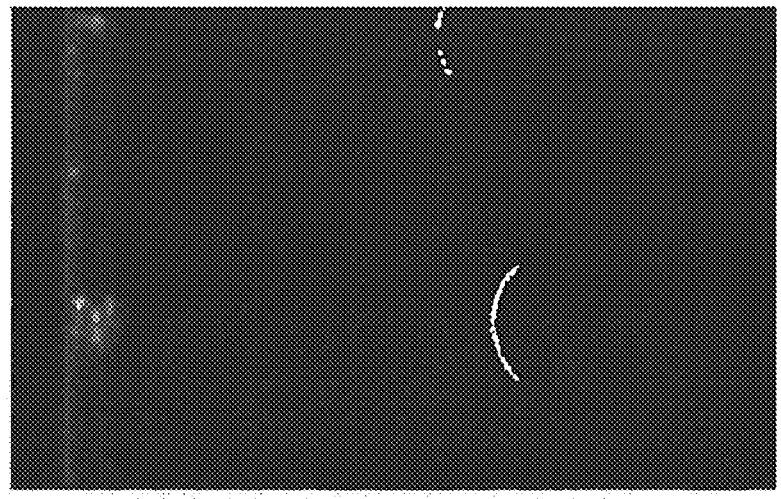

The particles in the nth multiplied binary image may be identified (550) as super-elevation particles. FIG. 5d is one example of a multiplied binary image in which the particles have been identified (550) as super-elevation particles. These identified super-elevation particles may be associated with the additive manufacturing step of selectively melting (120) the metal powder.

The identified super-elevation particles in the nth multiplied binary image may be mapped (650). The mapping step (650) may include determining a location of each super-elevation particle in the nth multiplied binary image. In one embodiment, the location of a super-elevation particle may be determined via the coordinates of the pixels that make up that particle. The mapping step (650) may include determining the size of each super-elevation particle. The size of a super-elevation particle may be measured via the total number of pixels that make up the super-elevation particle. The mapping step (650) may include correlating the location and/or size of each super-elevation particle to a respective location in the powder bed. In one embodiment, the coordinates of the super-elevation particle in the binary image may be used in conjunction with one or more landmarks in the image, such as the building platform, in order to map the super-elevation particle to a location in the powder bed and/or metal body. Thus, x, y spatial coordinates of the super-elevation particle (e.g., relative to the building platform) may be determined. The z coordinate of the super-elevation particle in the powder bed may be determined, for example, via the layer number of the powder layer and/or metal layer and knowledge of a pre-determined layer thickness.

An nth layer of a three-dimensional volume quality model may then be created (750) based at least in part on the mapped super-elevation particles. In one embodiment, a two-dimensional contour of the nth metal layer of the metal body may be generated from a pre-designed three dimensional CAD (computer-aided design) model. Then, the location and/or size of each super-elevation particle may be integrated into the two-dimensional contour. An nth layer of the three-dimensional volume quality model may then be created based at least in part on the integrated two-dimensional contour.

The above steps (120 through 750) may be repeated (850) until the metal body and its corresponding three-dimensional volume quality model are complete.

Figure 7:
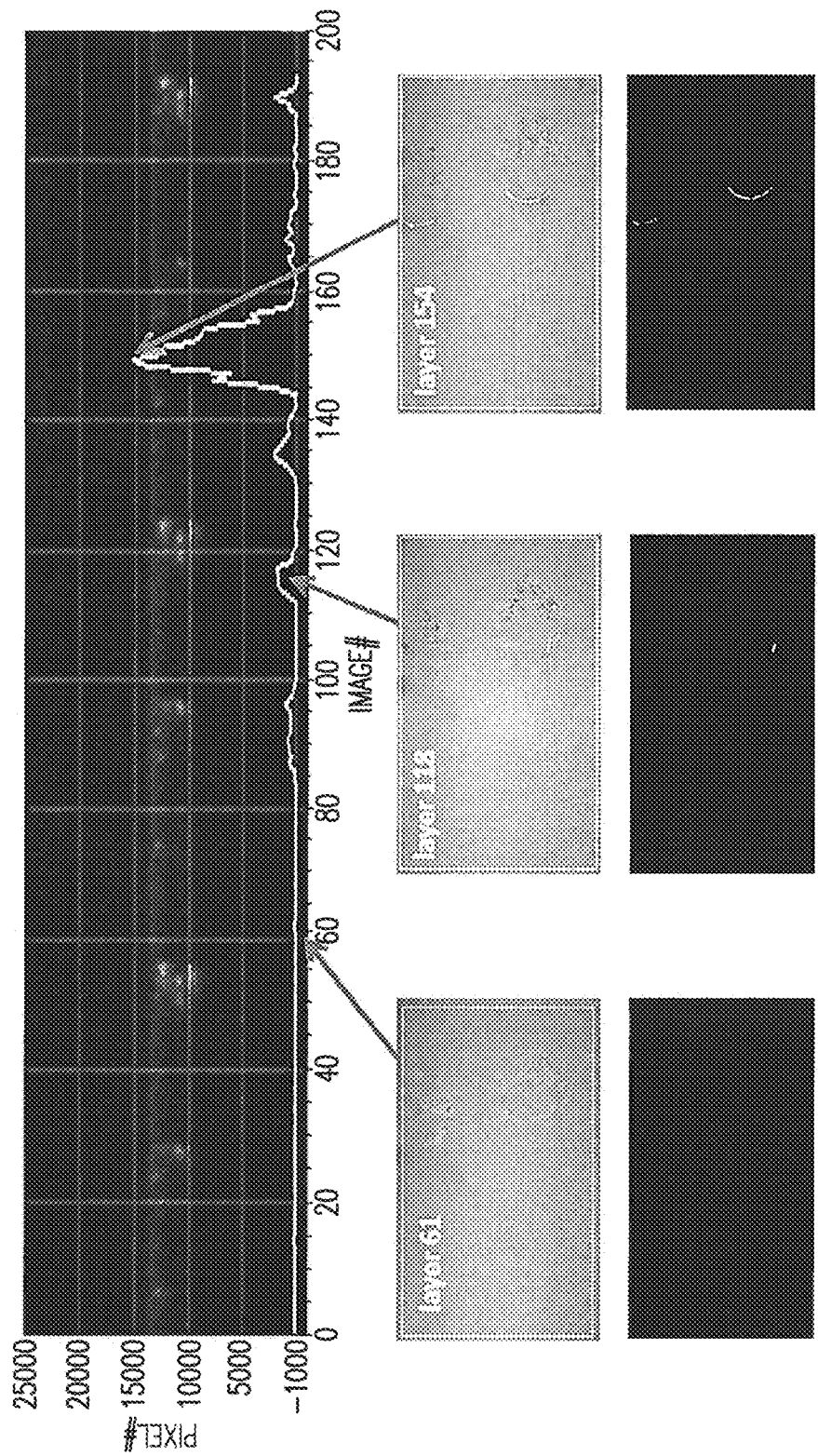
FIG. 7 is an example of a time-series chart showing the amount of super-elevation detected in each metal layer of a metal body.

Referring now to FIG. 7, as an alternative or in addition to a three dimensional VQM of the super-elevation, a time-series chart of the super-elevation particles detected at each metal layer (i.e., for layers n=1, 2, . . . N) may be created. Specifically, a total number of on-pixels may be determined for the identified (550) super-elevation particles detected at each metal layer. Thus, the total number of on-pixels comprising the super-elevation particles of each multiplied binary image may represent the total amount of super-elevation detected at the respective layer of metal powder.

Figure 4:
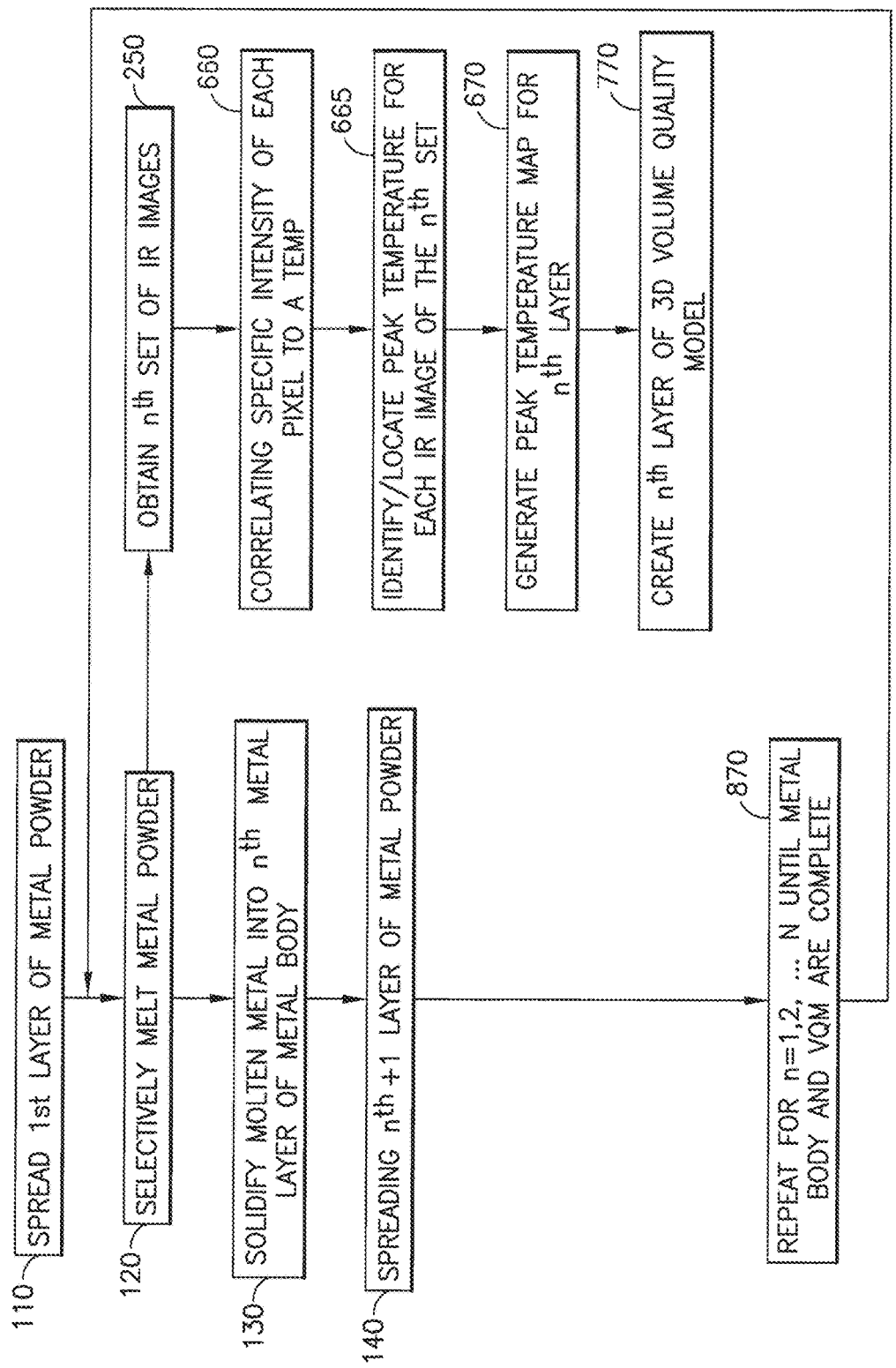
FIG. 4 is a schematic illustration of one embodiment of a method for creating three-dimensional volume quality models based on generated peak temperature maps in additively manufactured metal bodies.

Referring now to FIG. 4, one embodiment of a method for creating three-dimensional volume quality models based on generated peak temperature maps is illustrated.

In the illustrated embodiment, a first metal layer of a metal body may be additively manufactured. In this regard, the first layer of metal powder may be spread (110) on the powder bed. At least a portion of the metal powder may be selectively melted (120), thereby forming a melt pool of molten metal. The molten metal may be solidified (130) into the nth (e.g., the first) layer of the metal body. Then, the nth+1 (e.g., the second) layer of metal powder may be spread (140) the on the powder bed, thereby covering the first metal layer of the metal body with powder.

Concomitant to the selectively melting step (120), an nth (e.g., a first) sequential set of infrared images of the melt pool may be obtained (250). The nth sequential set of infrared images may also include at least a portion of the powder bed and/or the build platform. The nth sequential set of infrared images may be obtained, for example, via a digital video camera equipped with an optical filter that passes only near-infrared (NIR) energy. As used herein an "infrared image" is a digital image that depicts infrared radiation.

The specific intensity value of each pixel of each infrared image of the nth sequential set of infrared images may be correlated (660) to a temperature.

Figure 8B:
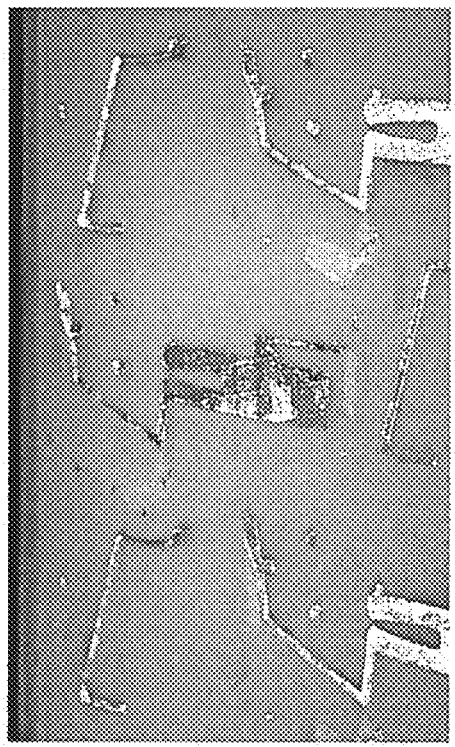
Figure 8A:
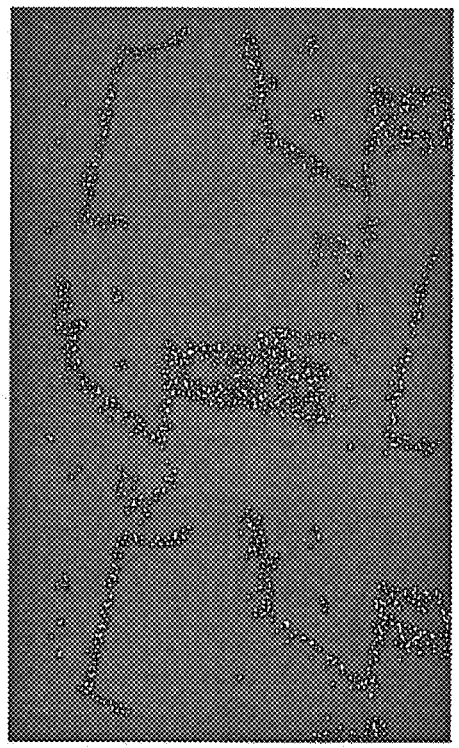
FIG. 8a is an illustration of one embodiment of a temperature map of the $n^{th}$ metal layer of several metal bodies.

The peak temperatures in the nth sequential set of infrared images may be mapped (670). The mapping step (670) may include determining a peak temperature point in each infrared image of the nth sequential set of infrared images. As used herein, a "peak temperature point" is the pixel of an infrared image that represents the highest temperature in that infrared image. The mapping step (670) may include determining the location of the peak temperature point in each infrared image of the nth sequential set of infrared images (665). The mapping step (670) may include correlating the location of each peak temperature point to a respective location on the first metal layer of the metal body, thereby creating a peak temperature map of the nth metal layer of the metal body. In one embodiment, the coordinates of the peak temperature point in the infrared image may be used in conjunction with one or more landmarks in the image, such as the building platform and/or metal body itself in order to map the peak temperature point to a location on the metal body. Thus, x, y spatial coordinates of the peak temperature point (e.g., relative to the building platform and/or metal body) may be determined. The z coordinate of the peak temperature point in the powder bed may be determined, for example, via the layer number of the powder layer and/or metal layer and knowledge of a pre-determined layer thickness. FIG. 8a is an illustration of a peak temperature map of the nth metal layer of several metal bodies being additively manufactured concurrently in the same powder bed. FIG. 5b is a digital image of the nth metal layer of the metal bodies.

An nth layer of a three-dimensional volume quality model may then be created (770) based at least in part on the mapped peak temperature points. In one embodiment, a two-dimensional contour of the nth metal layer of the metal body may be generated from a pre-designed three dimensional CAD (computer-aided design) model. Then, the location of each peak temperature point may be integrated into the two-dimensional contour. An nth layer of the three-dimensional volume quality model may then be created based at least in part on the integrated two-dimensional contour. FIG. 9a is an illustration of a peak temperature map of the nth metal layer of a metal body. FIG. 9b is a digital image of the nth metal layer of the metal body. FIG. 9c is an illustration of a two-dimensional contour of the nth metal layer of the metal body of FIG. 9a in which the peak temperature points have been integrated onto the two-dimensional contour.

The above steps (120 through 770) may be repeated (870) until the metal body and its corresponding three-dimensional volume quality model are complete. The VQM of the metal body based on the peak temperature points may facilitate detection and mapping of non-uniform temperature distribution, voids in the metal body, porosity, lack of fusion, and/or potential delamination of layers within the metal, among others. In another embodiment, the nth sequential set of infrared images may be analyzed in order to determine one or more of cooling rate, molten pool size, and/or heat transfer characteristics.

Figure 10:
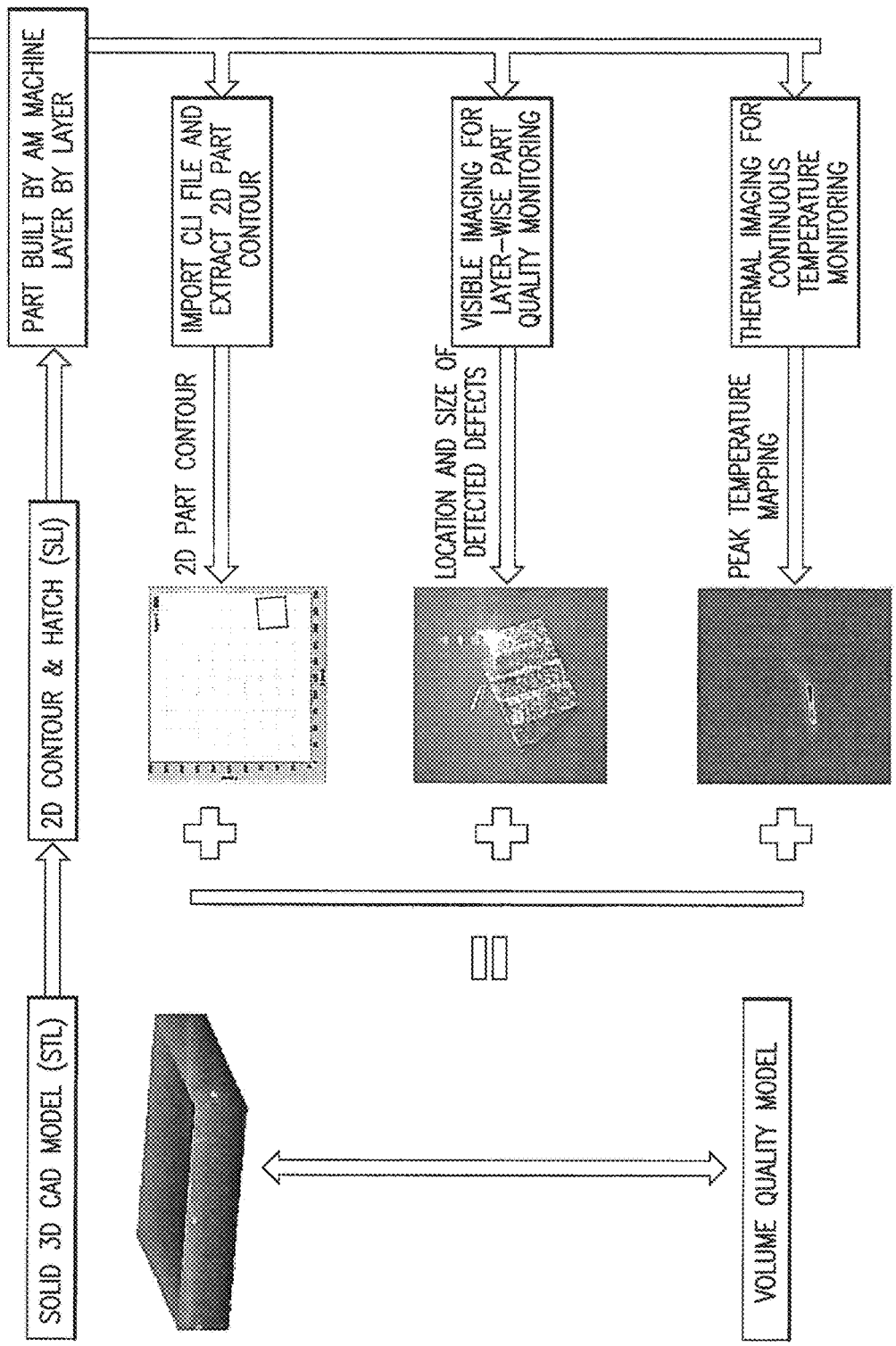
FIG. 10 is a schematic of one embodiment of a method of creating a volume quality model in accordance with the instant disclosure.
Figure 11:
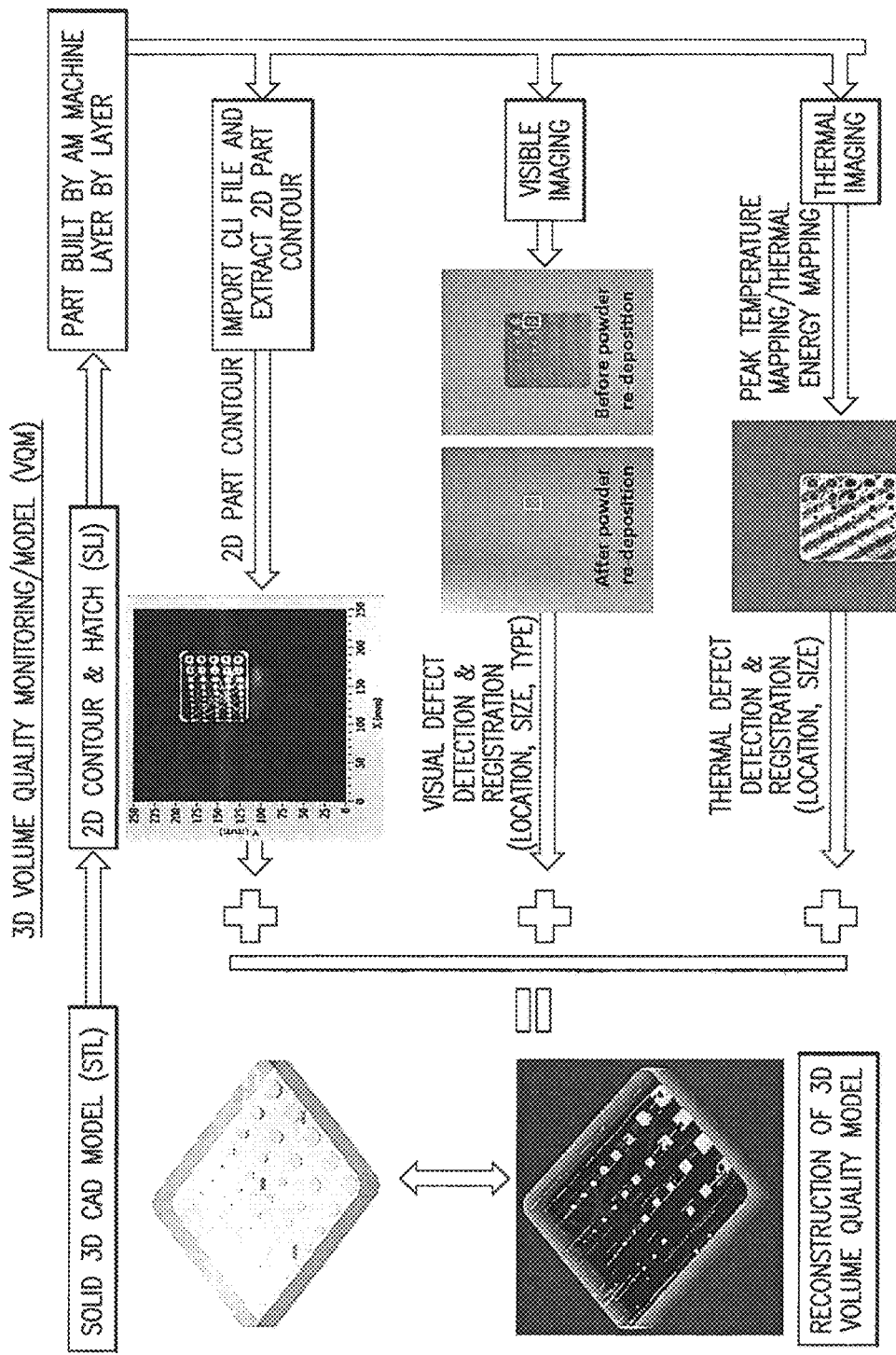
FIG. 11 is a schematic of another embodiment of a method of creating a volume quality model.
Figure 13B:
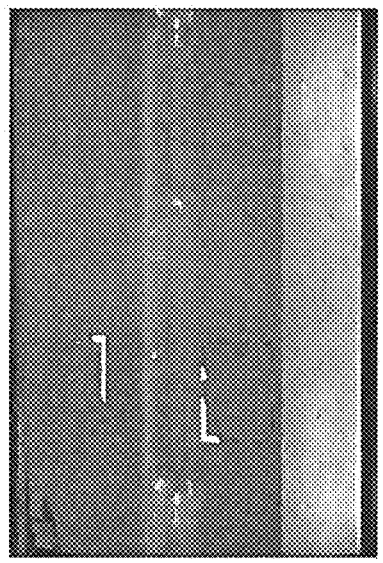
FIG. 13A-D depicts a sequence/progression of obtaining visible images (e.g. via a digital camera configured to take images in the visible spectrum), where 13A and 13B are successive views of an additive manufacturing part build.
Figure 13D:
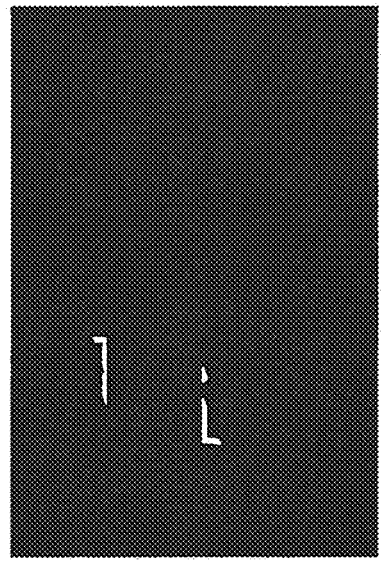
Figure 13A:
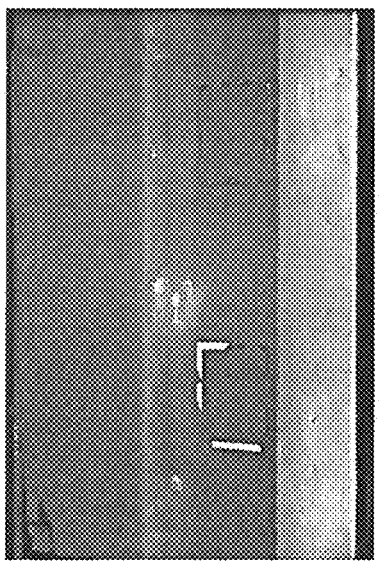
Figure 13C:
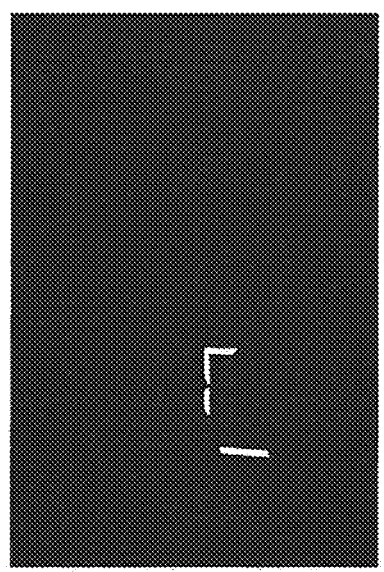
Figure 14B:
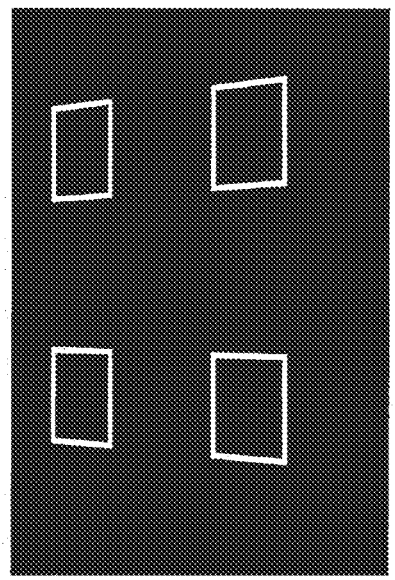
FIG. 14A-B is an example depicting the sequence/operation of adding subsequent thresholded images together to create a "partial" added visible image (FIG. 14A, which depicts FIG. 13C added to FIG. 13D) and a "complete" added visible image (FIG. 14B), depicting the entire calibration pattern built, illustrating the perspective distortion of the visible camera, based on the position (angle) of the visible camera compared the machine position (e.g. plan view, as in FIG. 12).
Figure 14A:
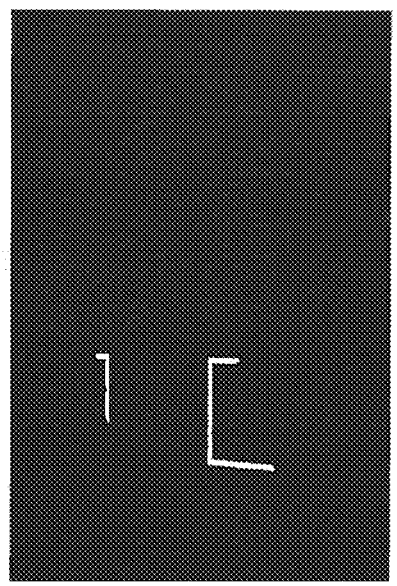
Figure 15A:
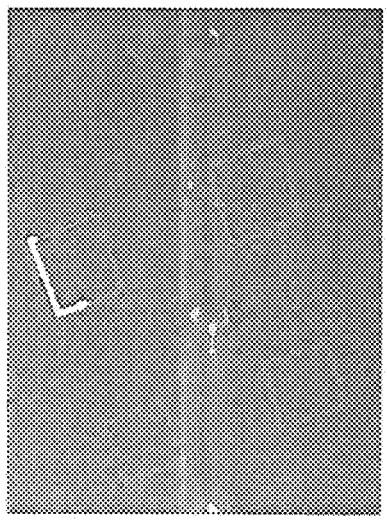
FIG. 15A-D depicts a sequence/progression of obtaining thermal images (e.g. via a thermal camera configured to take thermal images), where 15A and 15B are successive views of an additive manufacturing part build.
Figure 15B:
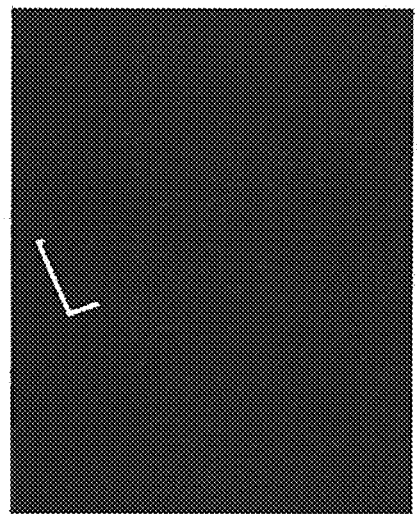
Figure 15C:
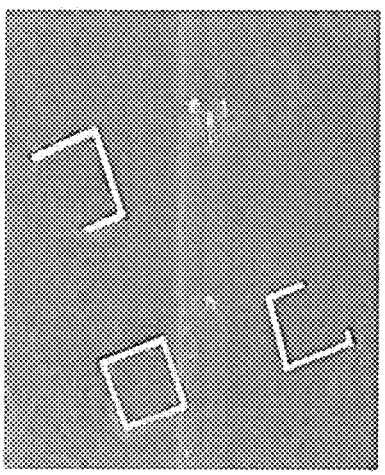
Figure 15D:
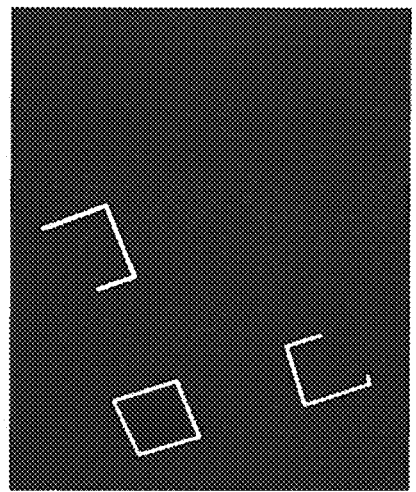
Figure 16B:
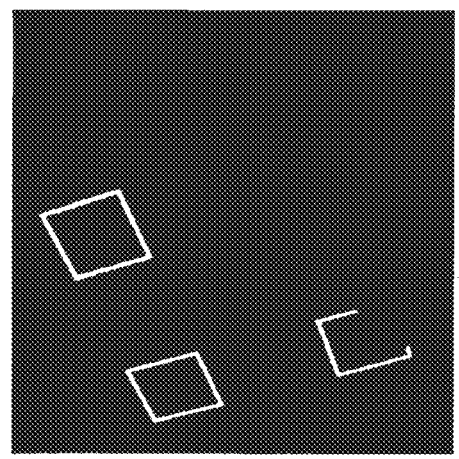
FIG. 16A-B depicts an example of the sequence/operation of adding subsequent thresholded images together to create a "partial" added thermal image (FIG. 16A, which depicts FIG. 15C added to FIG. 15D) and a "complete" added thermal image (FIG. 16B), depicting the entire calibration pattern built, illustrating the perspective distortion of the thermal camera, based on the position (angle) of the thermal camera compared the machine position (e.g. plan view, as in FIG. 12).
Figure 16A:
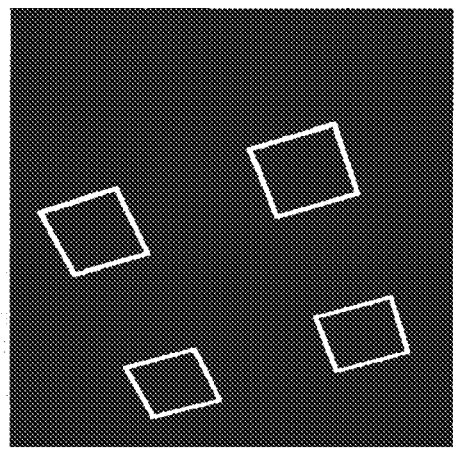
Figure 17B:
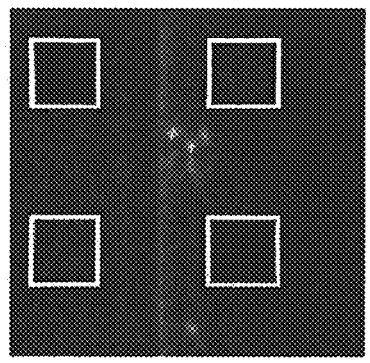
FIG. 17A-D depict an operation (sub-step) of the calibration method in accordance with the instant disclosure.
Figure 17D:
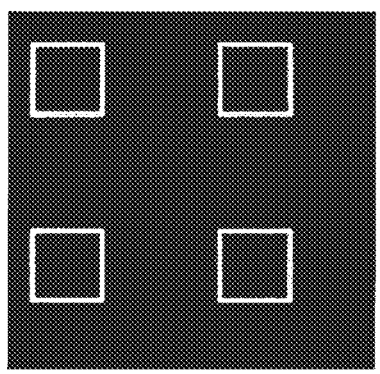
Figure 17A:
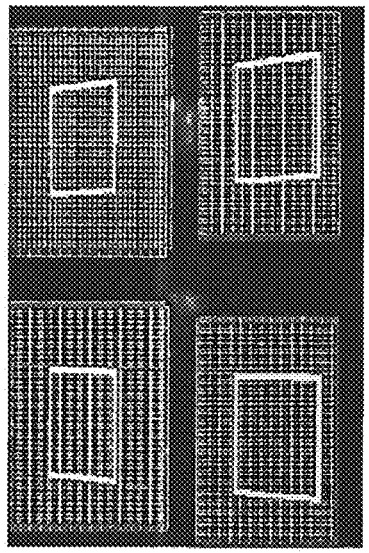
Figure 17C:
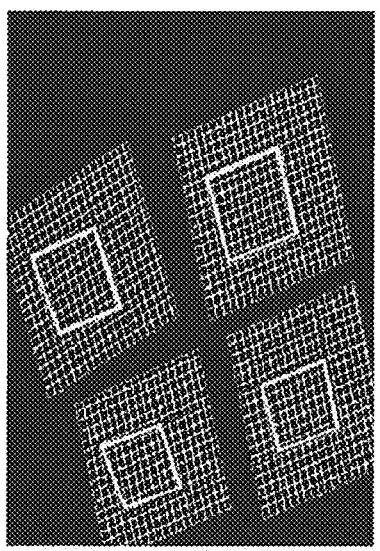

The above features (e.g., drag detection, super-elevation detection, and/or peak temperature mapping) may be combined into a single three-dimensional volume quality model. FIG. 10 is a schematic of one embodiment of a method of creating a volume quality model in which drag detection, super-elevation detection, and thermal features (e.g. peak temperature mapping) is combined to produce the volume quality model. Thus, the metal body may be visualized, via computer display, with potential drag defects, super-elevation defects and/or non-uniform peak temperature distribution from the 2D data collection overlaid on the model.

In some embodiments, the VQM is provided in a feedback viewable by an AM operator (or as an input into an AM control system/computer processor) such that an AM build can be aborted based on the partial VQM (corresponding to the partial AM build) in instances where the VQM identifies defects that are significant and cannot be corrected with changes in the AM build parameters. In some embodiments, the VQM model is configured to provide a yellow-flag or red-flag alert to the control system and/or user in instances where a defect is noted (not necessarily resulting in a "fail" part) vs. a significant defect is noted (e.g. resulting in a part that fails the specifications for that particular part application).

In one embodiment, one or more of the cameras utilized to create the VQM are positioned different from the plan view of the AM part build (e.g. as viewed by the machine perspective). As such, the cameras have perspective distortion as compared to the machine perspective and to each other (visible vs. thermal cameras). In some embodiments, perspective distortion is due to the position and/or view angle of the digital camera.

In one or more embodiments of the instant disclosure, the camera(s) is/are calibrated to reduce and/or eliminate perspective distortion, such that the resulting VQM includes inputs (images) from the visible and thermal cameras that are corrected for perspective distortion and/or are readily combinable with each other and/or with the AM machine perspective.

In one embodiment, a method of calibrating the AM system (with AM machine, visible camera, and thermal camera configured to create a three dimensional volume quality model) is provided. In one embodiment, the method includes: capturing with a camera successive images during AM build of a calibration build part (e.g. having a unique pattern including a plurality of readily identifiable features); thresholding the images with a processor to depict the part image only; adding thresholded images together with a processor to create an image of the entire calibration part build; obtaining the x,y coordinates/coordinate points of the calibration build part (e.g. unique pattern and/or features of the calibration part build, i.e. corner points on a square calibration build pattern); extracting the x, y coordinates for the calibration build having the camera perspective; comparing the coordinates for the calibration build having the camera perspective with the machine coordinates; creating a correction factor with a processor including a perspective transformation matrix; correcting the camera perspective to a corrected camera perspective with the perspective transformation matrix to provide corrected camera coordinates compatible with the machine coordinates.

In some embodiments, the method further comprises integrating the corrected camera coordinates with the machine coordinates to provide one set of coordinates including information obtained from (filtered, extracted, and or processed form) the camera images.

In some embodiments, the obtaining step includes detecting the edge(s) of the calibration build part in the camera perspective view.

In some embodiments, an AM machine (configured to utilize powder-based AM techniques and processes) is configured with a thermal camera and a visible cameras are provided. For example, the thermal camera is configured from a digital CCD Gigabit Ethernet camera, along with a notch filter blocking the wavelength of the laser of the additive manufacturing machine, a near-infrared band-pass filter, and one neutral density filter. As another example, the visible camera is configured from a digital CCD Gigabit Ethernet camera, along with polarizer and focus lens. As the AM machine builds the calibration build part having a specified pattern (e.g. of known dimensions) the cameras are calibrated according to one or more of the instant methods to a common coordinate system. The pattern of the calibration build part, of known dimensions, allows the two camera system coordinate systems to be transformed to a common machine coordinate system. This allows all of the systems (cameras and machine) to operate with a common coordinate system. Thus, the two cameras capture continuous images during the AM building process and are able to compile information indicative of defects or other features into a single machine coordinate system while also removing any perspective distortion in the camera images.

Thus, as a layer is built, the cameras are configured and synchronized to the additive machine such that calibrated (corrected) visible images and calibrated (corrected) thermal images are obtained. The visible and thermal images are processed via a processor for information (e.g. indicative of any defects) for a layer and the processed information is incorporated (processed) into a two dimensional file/map and saved to a registration list. Then, the registration list is compiled/processed to create a three dimensional volume quality model, which details the maps of any defects in any of the successive layers.

In some embodiments, the VQM is compared to the STL/cad model. In some embodiments, the VQM is compared to NDE analysis data.

In some embodiments, the VQM model is compared to analytical inspection results obtained by non-destructive evaluation methods (e.g. ultrasonic, x-ray, or CT inspection), to assist in interpreting the NDE results for defects.

In some embodiments, the VQM model is used in place of NDE analytical techniques to test a part and/or evaluate for defects, in situ, during the AM part build.

In some embodiments, the method includes a visible camera perspective. In some embodiments, the method includes a thermal camera perspective.

In some embodiments, one of the cameras is calibrated while the other camera is not calibrated and corrected.

In some embodiments, both cameras are calibrated and corrected for their perspectives, where the thermal camera and visible camera are different from each other, and where each of the thermal camera and visible camera are configured with different perspectives (e.g. where each perspective is a distorted perspective) than the machine perspective of the AM build platform (machine perspective, undistorted).

In some embodiments, the calibration method on a calibration part build is completed prior to the AM part build, such that each of thermal camera perspective distortion and visible camera perspective distortion are corrected to provide uniform coordinates (e.g. integrated with the machine perspective into one set of coordinates), such that the cameras are calibrated to provide inputs readily processed via a processor to yield/create one or more embodiments of a three dimensional volume quality model in accordance with the instant disclosure. In this embodiment, the corrected perspective yields a corrected digital image (e.g. series of coordinates) such that the location of each image pixel is related to a respective location in the powder bed in a uniform matter for each camera.

While reference is made to digital cameras, it is noted that the various embodiments can be completed with video cameras (a series of stills) and/or non-digital cameras (e.g. using film to capture the image).

Figure 18:
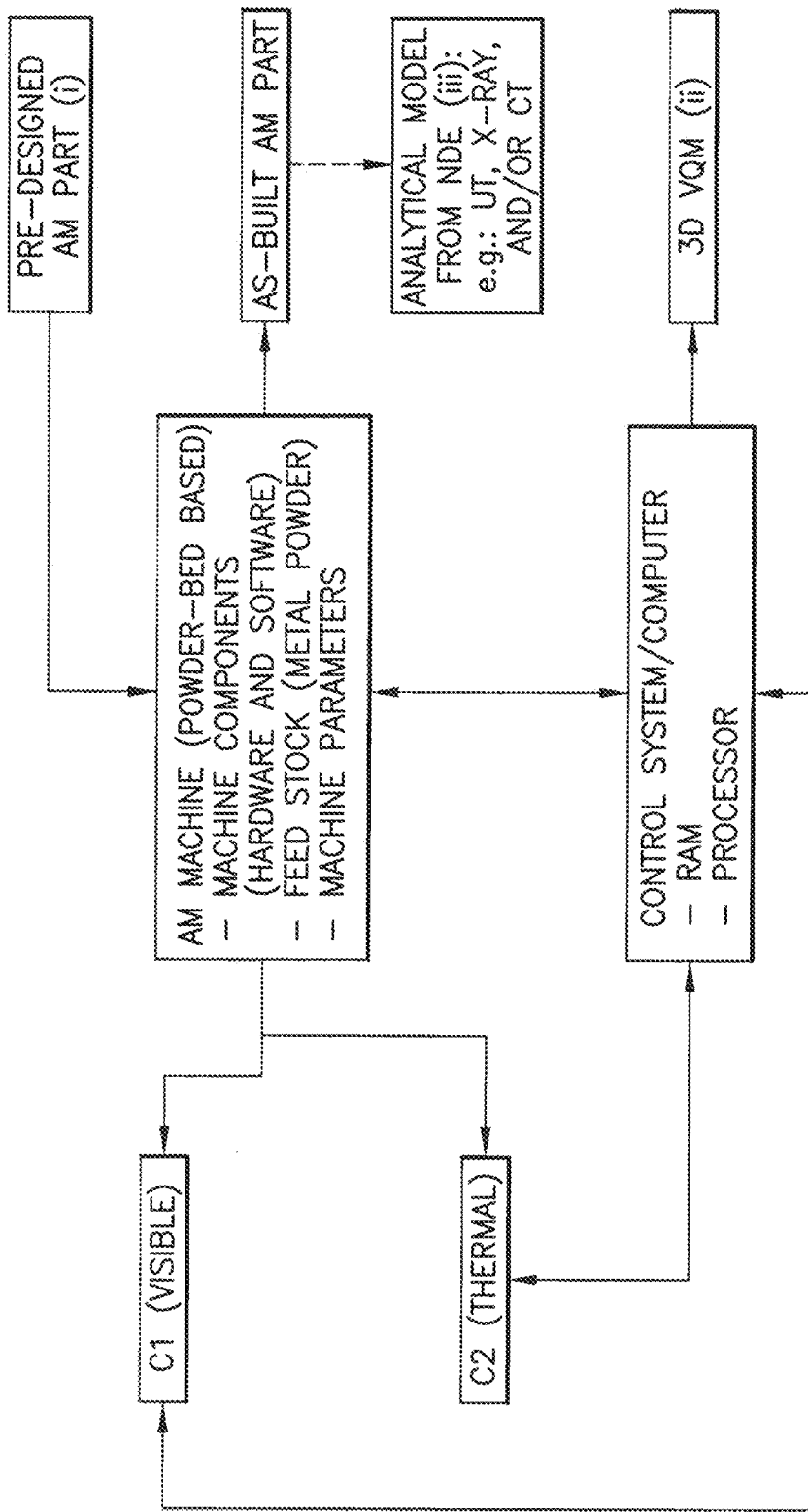
FIG. 18 is an embodiment of a schematic of a system in which one or more of the various methods in the instant disclosure can be performed. An additive manufacturing machine (e.g. powder bed based) is provided with its components, feed stock/material (metal powder), and operating parameters. Two cameras, C1 (e.g. digital camera, including components (filters, optics, wiring, etc) configured to obtain images of the AM build process in visible image form) and C2 (e.g. digital camera, including components (filters, optics, wiring, etc.) configured to obtain images of the AM build process in thermal image form) are configured to the AM machine such that the cameras obtain digital images synchronized with respect to the AM build (e.g. iteratively, layer by layer, as feed stock is transformed into AM part build layer). The control system/computer is connected to C1, C2, and the AM machine, such that the control system is configured to communicate with these items and create a three dimensional volume quality model from the images obtained and translated via the computer processor, algorithms and related modules in accordance with one or more embodiments of the instant disclosure. The AM machine is configured to receive information concerning a "pre-designed AM part" and translate the pre-designed AM part into an "as-built AM Part". The as-built AM part has properties based on the build parameters that may or may not correspond with the pre-designed AM part. Non-destructive evaluation techniques can be utilized to confirm how closely the as-built AM part corresponds to the pre-designed AM part and/or confirm the presence and/or prevalence of defects. Some non-limiting examples of NDE include ultrasonic testing, x-ray testing, and computer tomography scanning.
Figure 19:
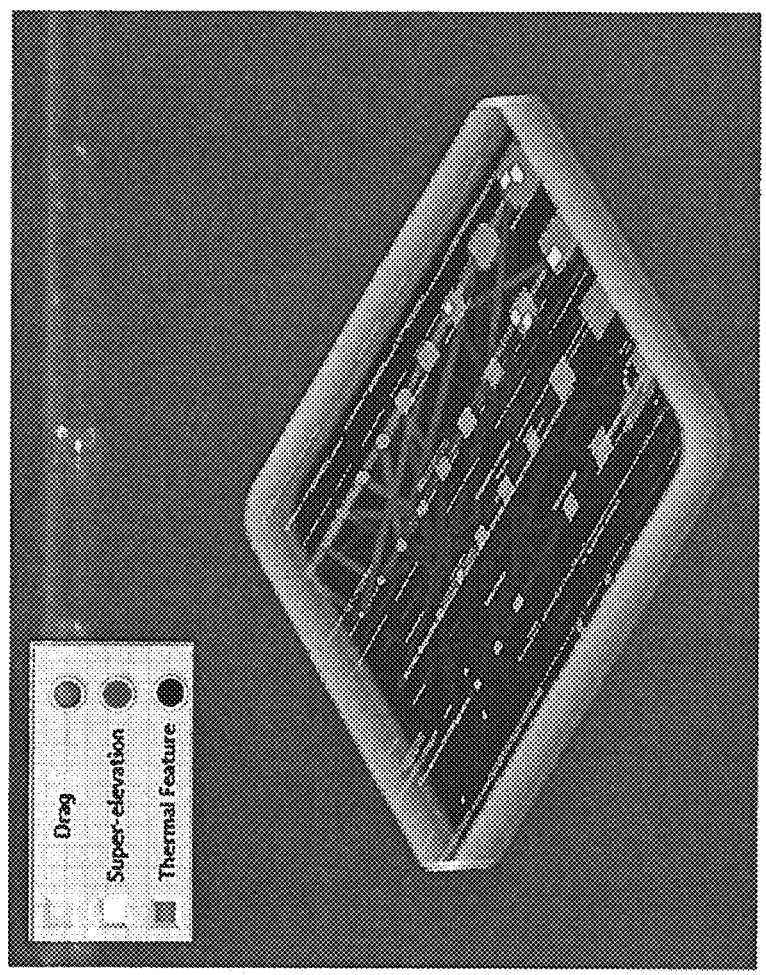
FIG. 19 is a perspective view of an embodiment of a volume quality model, depicting defects including drag, super elevation, and thermal features (cold spots) in the three dimensional AM part model.
Figure 20:
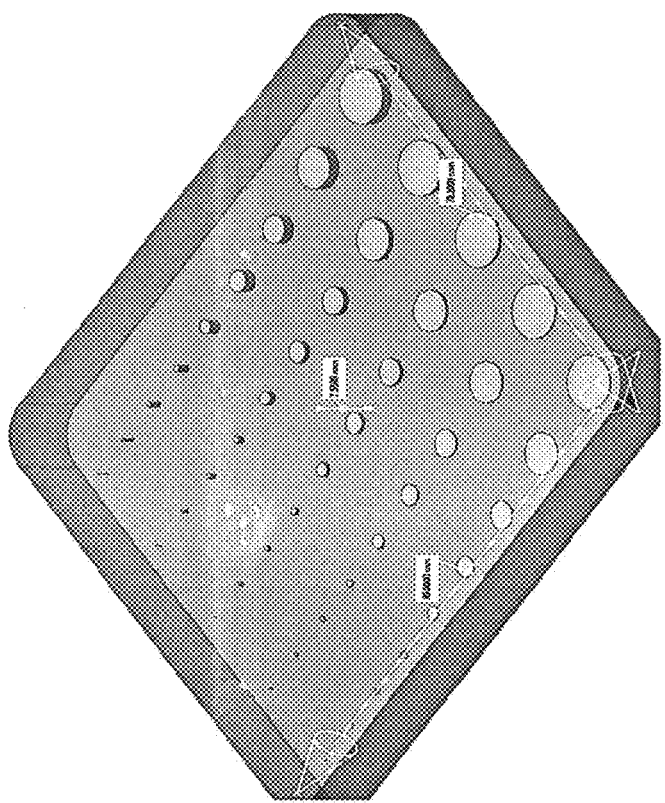
FIG. 20 is perspective view of a pre-designed AM part that is a CAD design of an AM part with features (defects) in the form of hollow-bodied cylinder shapes of varying diameters, where the metrics of the planned defects are outlined in the table on FIG. 20. This CAD model was used as an illustrative example (with corresponding details in FIGS. 20-30) to depict how closely/accurately the VQM could identify corresponding defects/features (planned and/or as a function of the AM build process) in the data obtained with one or more embodiments of the instant disclosure. The planned cylindrical features/defects began between layer 100 and 105 of the AM part build.
Figure 21:
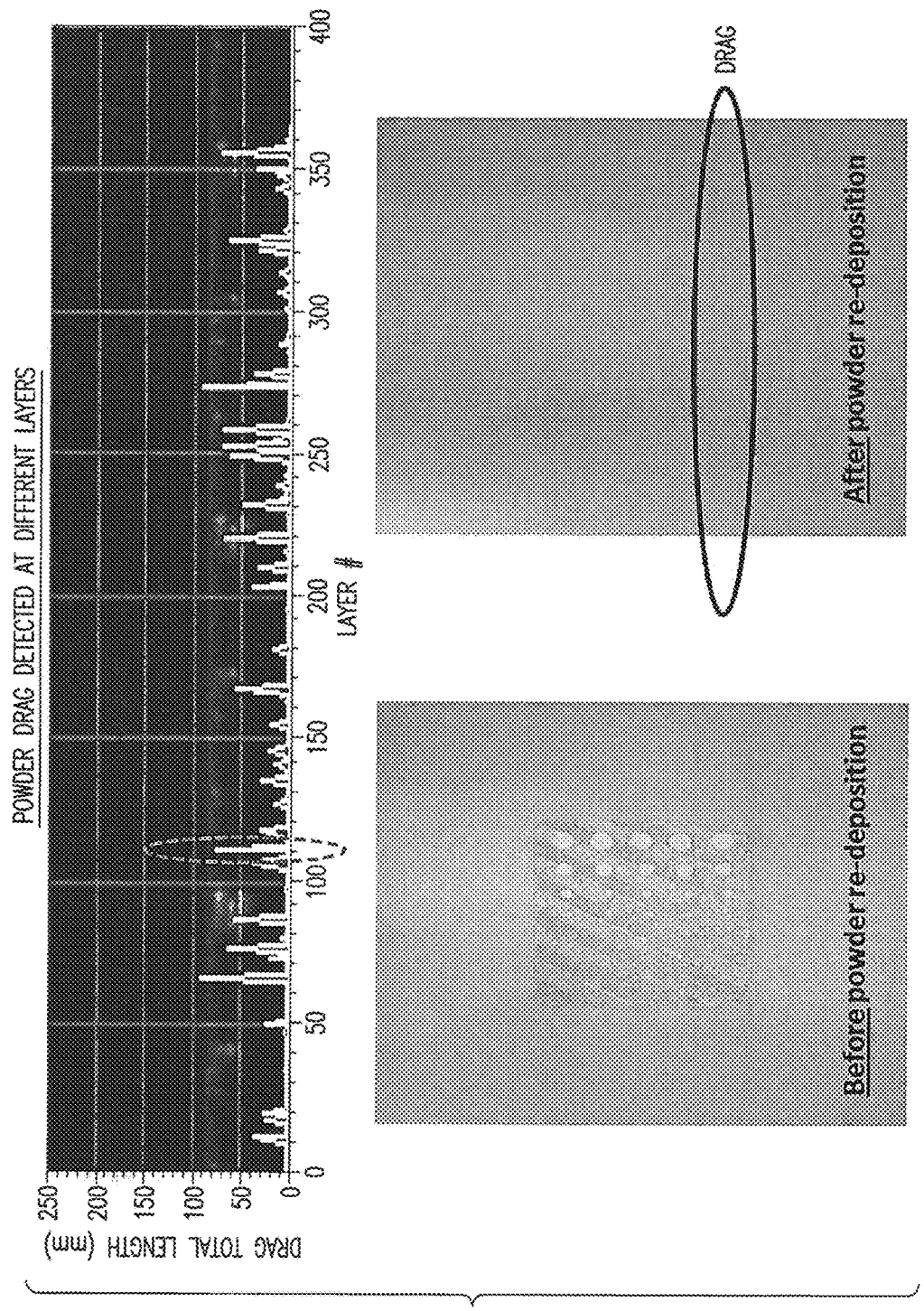
FIG. 21 is a chart depicting the total length of drag (in mm) for each layer (layer # in the part build) for a total of around 370 layers. Beneath the chart are two photographs, depicting the AM part surface (before powder redistribution) and after powder re-distribution (corresponding with the drag circled on the above-chart between layer #110 and #115).
Figure 22:
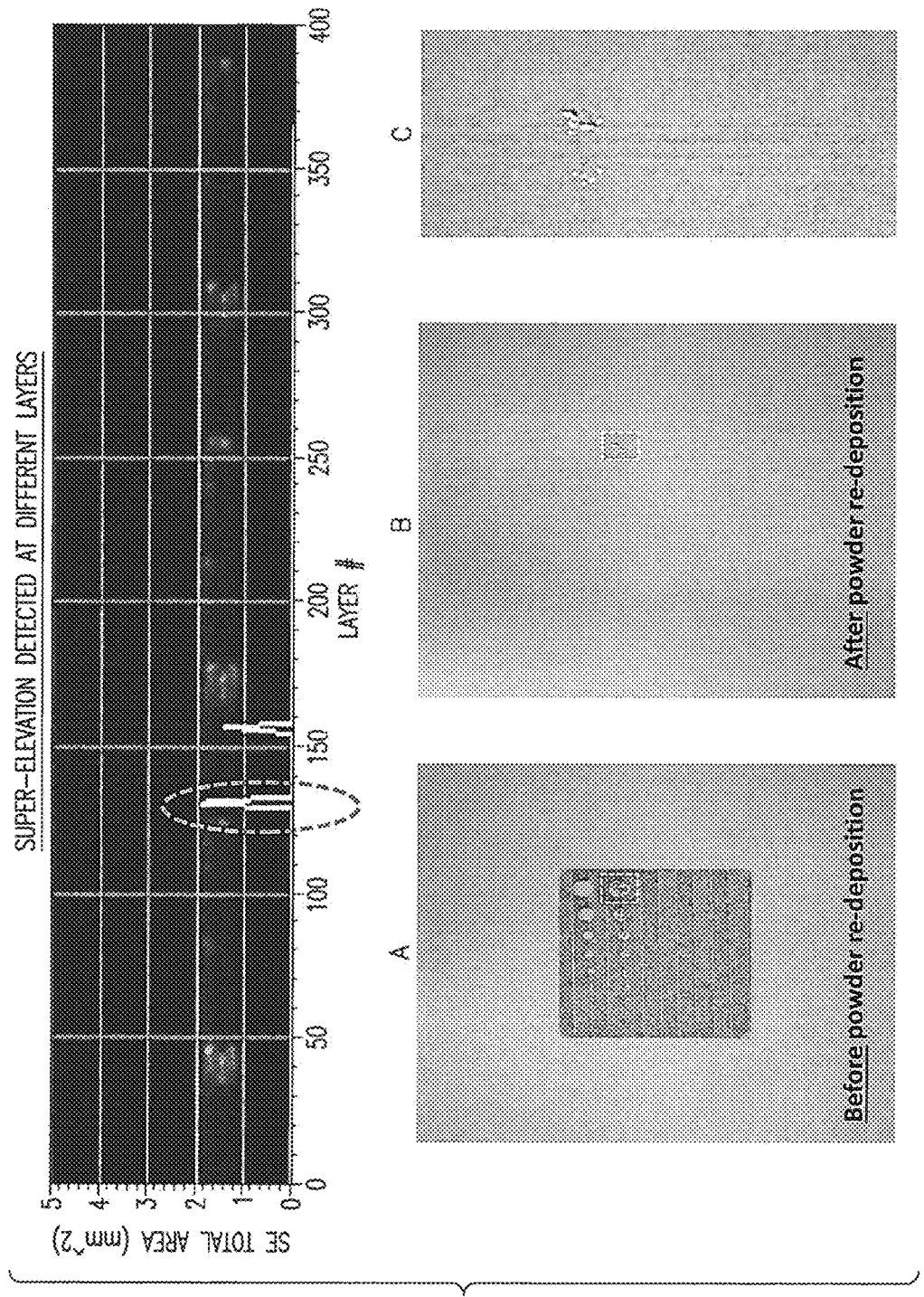
FIG. 22 is a chart depicting the super elevation area (in mm2) for each layer (layer # in the part build) for the same AM Part build in this illustrative example. Beneath the chart are three photographs, depicting the AM part surface (before powder redistribution) and after powder re-distribution (corresponding with the super elevation circled on the above-chart between layer #130 and #135). The other images (B and C) correspond to super elevation observable after powder re-distribution, depicting portions of the AM part (super-elevation points) that are poking through the powder deposited and corresponding to the next planned layer of AM build.
Figure 23:
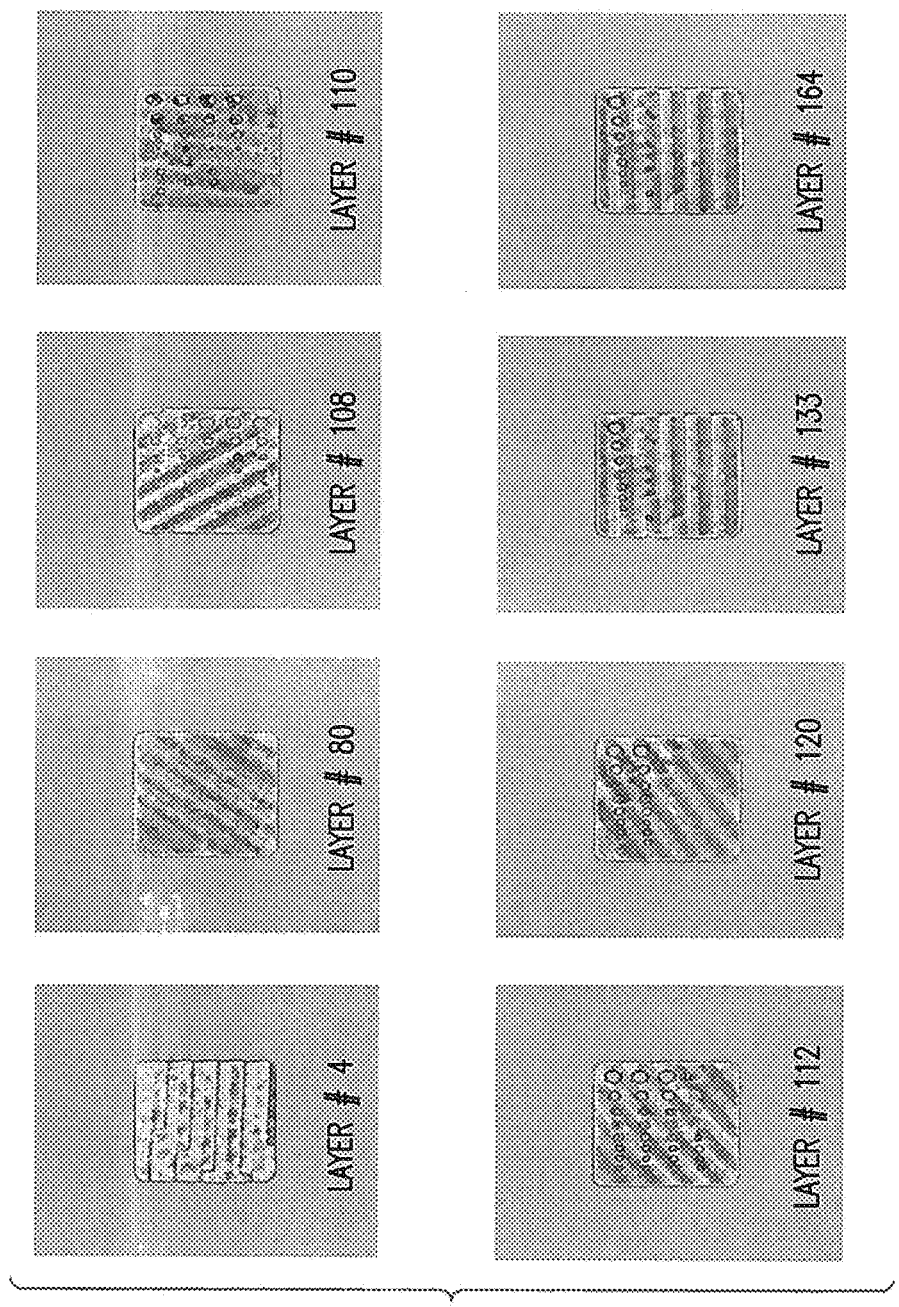
FIG. 23 depicts the thermal features (cold spots) detected at different layers of the part build, showing comparative thermal maps of layers 4, 80, 108, 110, 122, 120, 133, and 164 of the additive manufacturing layers of the part build.
Figure 24:
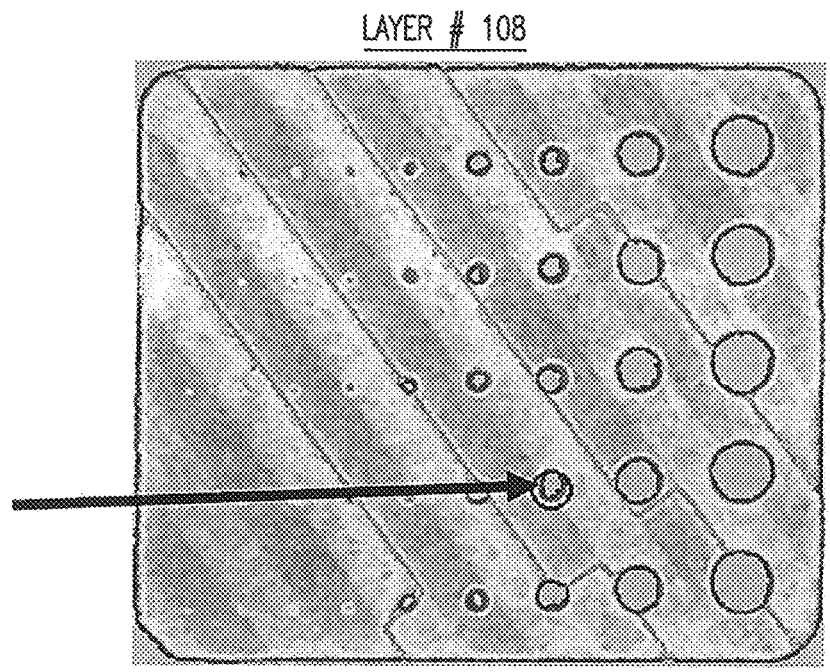
FIG. 24 is a close-up of the thermal map depicting thermal features of layer #108, where the arrow points to a location of interest/thermal feature (cold spot) identified with an embodiment of one or more of the present methods.
Figure 25:
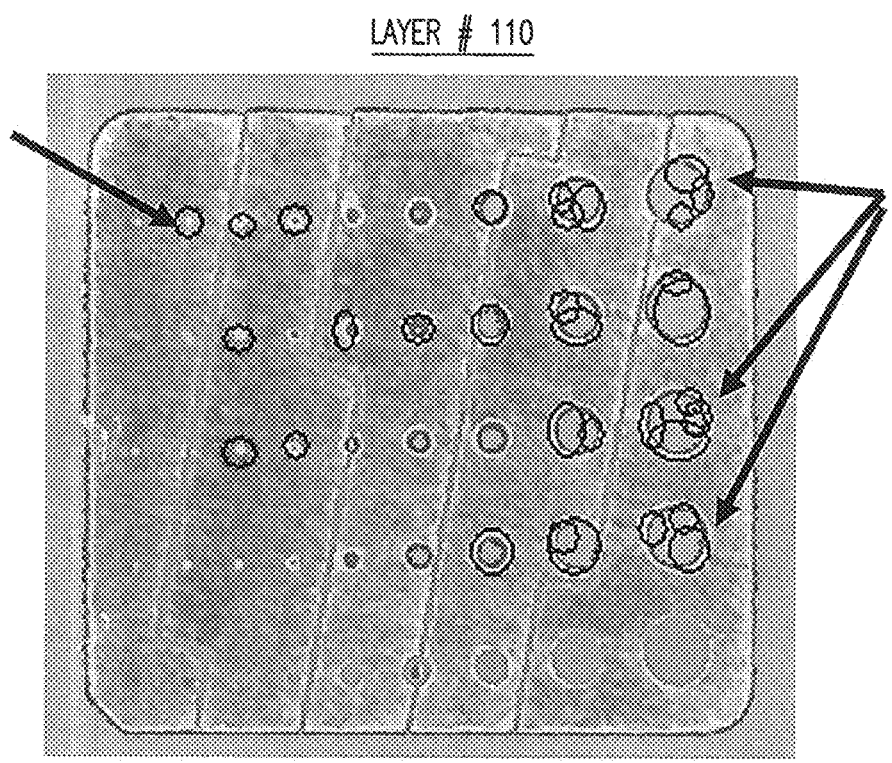
FIG. 25 is a close-up of the thermal map depicting thermal features of layer #110, where the arrows point to a location of interest/thermal feature (cold spot) identified with an embodiment of one or more of the present methods, where some locations include multiple cold spots (e.g. for larger defects in the build plan).
Figure 26:
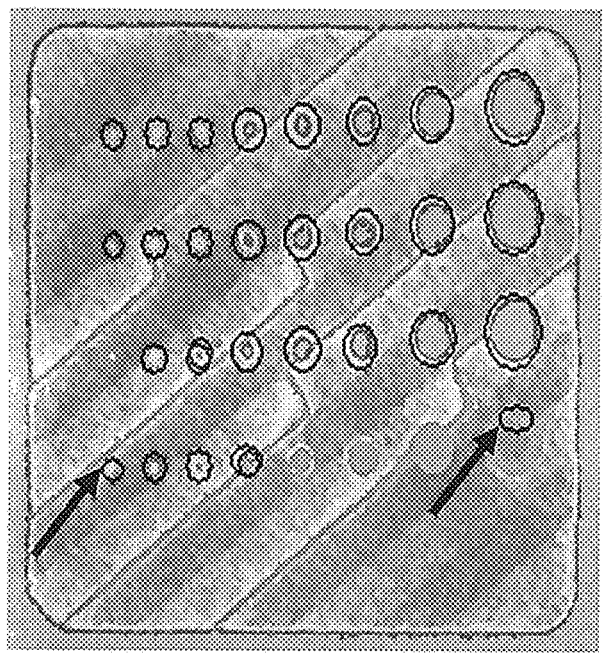
FIG. 26 is a close-up of the thermal map depicting thermal features of layer #112, depicting more thermal features (e.g. cold spots) as compared to layers #108 and #110, also depicting thermal features identified for some of the smaller planned defects in the AM part build and thermal defects identified for an entire large scale planned defect, as compared to multiple thermal features identified for a single planned defect in layer #110.
Figure 27:
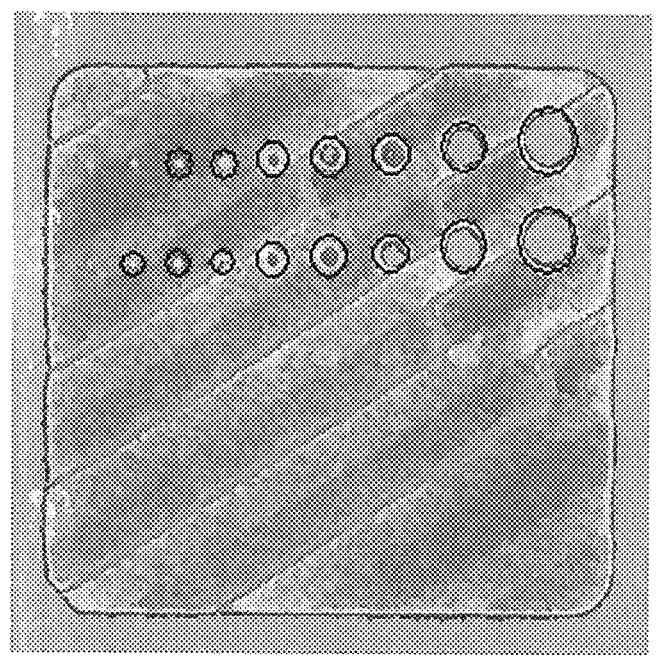
FIG. 27 is a close-up of the thermal map depicting thermal features of layer #120, depicting fewer thermal features as compared to layers #110 and #112, which is consistent with the location of the planned defects in the AM part.
Figure 28:
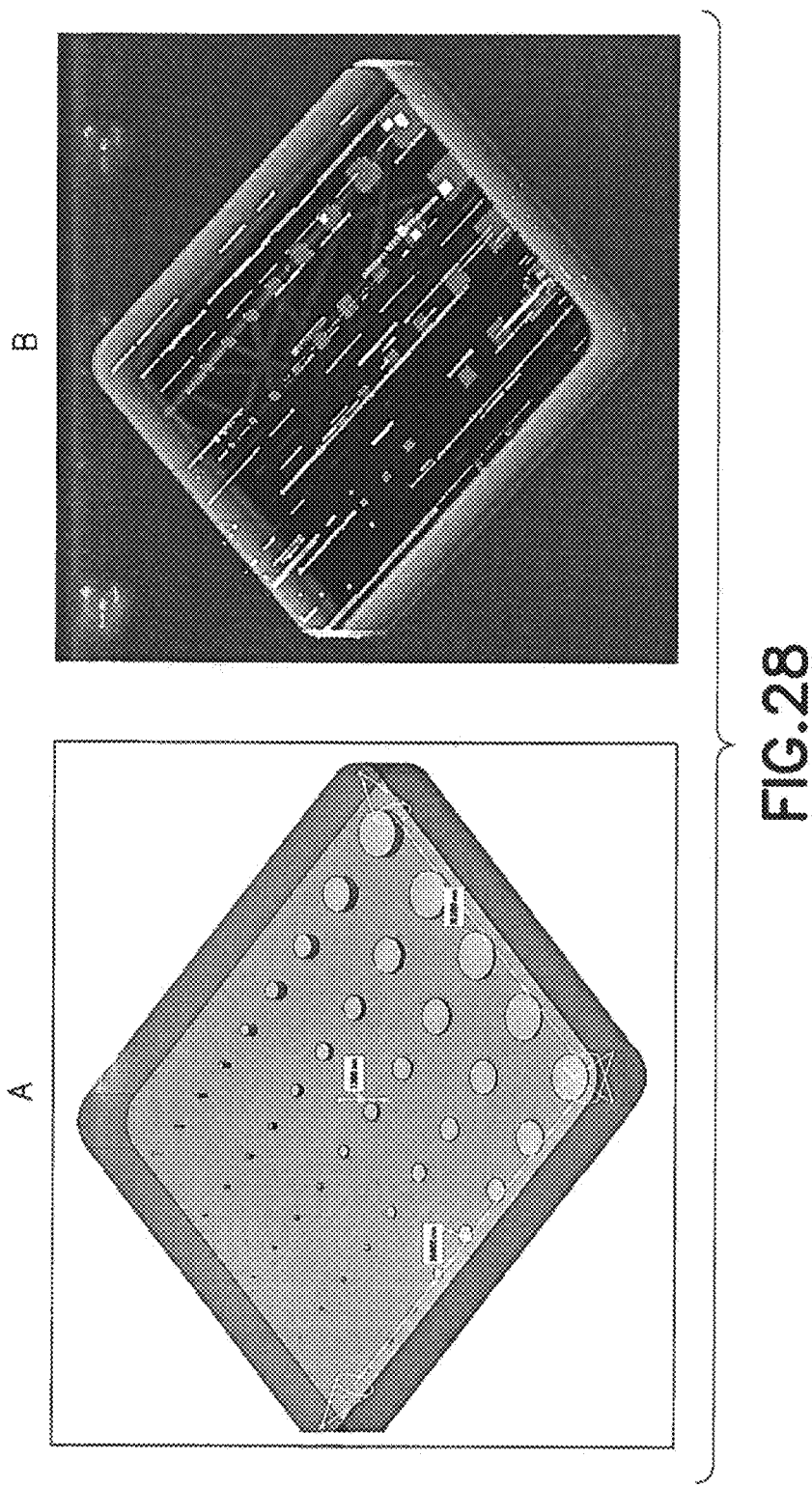
FIG. 28 depicts a comparison of a perspective view of A: the three dimensional CAD Model (pre-designed AM part) and a perspective view of B: the three dimensional volume quality model obtained with one or more methods of the instant disclosure. As visually observed side-by-side, the VQM closely corresponds to the three dimensional CAD model, while the VQM identifies cold spots corresponding to the planned defects in the CAD model, the VQM also identifies drag locations (depicted as striations along the various layers of the VQM) and super elevation points (e.g. several instances, generally coinciding with the locations of the larger planned defects).
Figure 29:
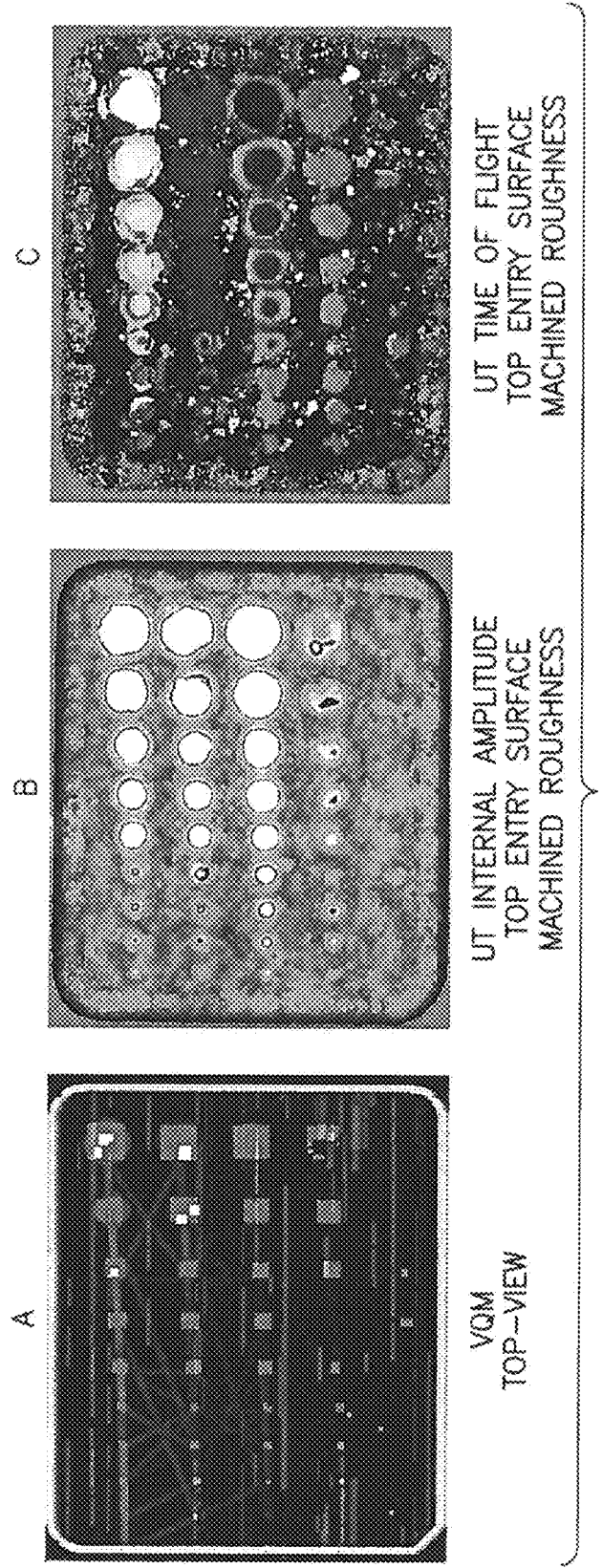
FIG. 29 is a top view of an embodiment of the volume quality model obtained through one or more of the methods herein, compared to analytical results received by non-destructive evaluation using ultrasound on the as-build AM part. As shown, the embodiment of A: VQM corresponds closely to the both ultrasound images including B: the ultrasound internal amplitude and C: ultrasound time of flight.
Figure 30:
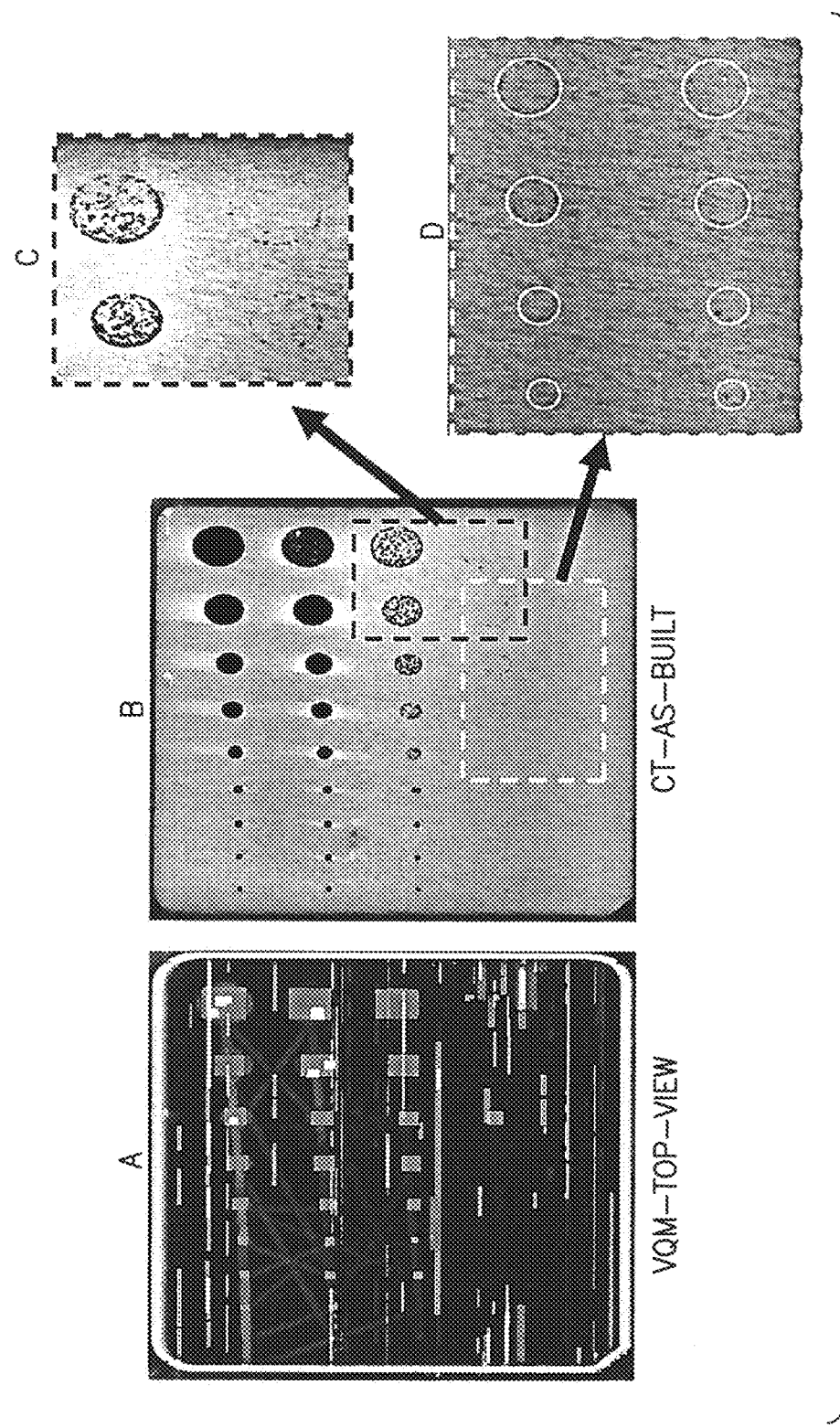
FIG. 30 is a top view of an embodiment of the VQM obtained in this example, as compared to analytical results received by non-destructive evaluation using computer tomography on the as-built AM part. As visually observed, (A) the VQM corresponds closely with (B) the CT of the AM part. Images C and D are close-up views of the CT, depicting some additional finer details regarding the planned defects. With the comparison of A and B, the VQM corresponds closely to the NDE analysis (CT) on the as-built part.

It is noted, with regard to the computer/control system (processor and/or memory) reference in FIG. 18 and throughout the application, the computer includes any such computing device capable of sending and receiving information/messages (e.g. over a network, to and from other computing devices (e.g. servers, etc.). Computing devices include laptops, personal computers, multiprocessor systems, microprocessor-based systems, network PCs, and/or programmable consumer electronics (e.g. cameras). The computer/control system can be configured wirelessly or with wires to enable communication between components and/or other computing devices. Of note, one or more of the embodiments described herein may be implemented using any appropriate computer system hardware and/or computer system software. In this regard, those of ordinary skill in the art are well versed in the type of computer hardware that may be used (e.g. mainframe, mini-computer, personal computer, network (intranet and/or internet), the type of computer programming techniques that may be used (e.g. object oriented programming) and the type of computer programming languages that may be used (e.g. lab view, C++, Basic, AJAX, Javascript, etc.). The aforementioned examples are illustrative and not restrictive. While various embodiments of the present disclosure have been described in detail, it is apparent that modifications and adaptations of those embodiments will occur to those skilled in the art. However, it is to be expressly understood that such modifications and adaptations are within the spirit and scope of the present disclosure.

What is claimed is:

1. A method comprising:
   (A) spreading a first layer of metal powder on a powder bed;
   (B) selectively melting at least a portion of the first layer of metal powder, thereby forming a melt pool comprising molten metal of the metal powder;
   (C) solidifying the molten metal into a first metal layer of a metal body;
   (D) spreading a second layer of metal powder on the first metal layer;
   (E) obtaining a first digital image of at least a portion of the second layer of metal powder;
     wherein the first digital image has a plurality of pixels;
     wherein each pixel of the plurality of pixels has a specific intensity value;
   (F) translating the first digital image into a first binary image, wherein the translating comprises:
     (i) determining a global average intensity value of the plurality of pixels;
     (ii) resetting any specific intensity value that exceeds a threshold value to be equal to the global average intensity value;
     (iii) determining a local average intensity value for said each pixel of the plurality of pixels;
     (iv) subtracting the specific intensity value of said each pixel of the plurality of pixels from the local average intensity value, thereby determining a background-corrected intensity value for said each pixel of the plurality of pixels;
     (v) replacing the specific intensity value of said each pixel with its determined background-corrected intensity value; and
     (vi) performing a thresholding operation on the first digital image, thereby creating the first binary image;
     wherein the first binary image has a plurality of binary pixels;
     wherein the plurality of binary pixels comprises particles; and
     wherein the particles are either drag particles or non-drag particles;
   (G) filtering the non-drag particles from the first binary image, wherein the filtering comprises:
     (i) performing an x-axis close operation on each of the binary pixels of the plurality of binary pixels;
     (ii) removing from the first binary image all particles having a particle width below a threshold width;

(iii) removing from the first binary image all particles having a particle elongation ratio below a threshold ratio;
(iv) performing a dilation operation on the first binary image;
(v) determining the number of on-pixels in each row of the first binary image;
(vi) determining the number of particles in each row of the first binary image,
(vii) switching any of the on-pixels to off-pixels for any pixels in a row of the first binary image, where the row of the first binary image has either a number of on-pixels less than a threshold on-pixel number, or a number of particles greater than a threshold particle number;
(H) identifying all remaining particles in the first binary image as the drag particles associated with the spreading a second layer step (D);
(I) mapping the drag particles associated with the spreading a second layer step (D), wherein the mapping comprises:
(i) determining a location of each of the drag particles in the first binary images;
(ii) determining a size of each of the drag particles, wherein a total number of pixels comprising each of the drag particles is representative of the size of each respective drag particle;
(iii) mapping the location and size of each of the drag particles to a respective location in the powder bed;
(J) creating a first layer of a three-dimensional volume quality model of the metal body based at least in part on the location and size of each of the drag particles associated with the spreading a second layer step (D).

2. The method of claim 1, wherein the creating step comprises:
generating a two-dimensional contour of the first metal layer of the metal body from a pre-designed three-dimensional model of the metal body;
integrating the location and size of each of the drag particles into the two-dimensional contour of the first metal layer; and
creating the first layer of the three-dimensional volume quality model of the metal body based at least in part on the integrated contour of the first metal layer.

3. The method of claim 2, wherein the two-dimensional contour of the first metal layer is extracted from a (common layer interface) file, and wherein the pre-designed three-dimensional model of the metal body comprises an STL file.

4. The method of claim 1, wherein the particles are first particles, wherein the non-drag particles are first non-drag particles, wherein the drag particles are first drag particles, and wherein the method comprises:
selectively melting at least a portion of the second layer of metal powder, thereby forming a melt pool comprising molten metal of the metal powder;
solidifying the molten metal into a second metal layer of the metal body;
spreading a third layer of metal powder on the second metal layer;
obtaining a second digital image of at least a portion of the third layer of metal powder;
translating the second digital image into a second binary image;
filtering second non-drag particles from the second binary image
identifying all remaining second particles in the second binary image as second drag particles associated with the spreading a third layer step;
mapping the second drag particles, thereby determining a location and size of each of the second drag particles associated with the spreading a third layer step;
creating a second layer of the three-dimensional volume quality model of the metal body based at least in part on the location and size of each second drag particle associated with the spreading a third layer of metal powder step.

5. The method of claim 1, wherein the performing a thresholding operation step (F)(vi) comprises performing an interclass variance thresholding operation on the first digital image.

6. A method comprising:
(A) spreading an $n^{th}$ layer or of metal powder on a powder bed;
(B) selectively melting at least a portion of the $n^{th}$ layer of metal powder, thereby forming a melt pool comprising molten metal of the metal powder;
(C) solidifying the molten metal into an $n^{th}$ metal layer of a metal body;
(D) spreading an $n^{th}+1$ layer of metal powder on the $n^{th}$ metal layer;
(E) obtaining an $n^{th}$ digital image of at least a portion of the $n^{th}+1$ layer of metal powder;
(F) first translating the $n^{th}$ digital image into an $n^{th}$ primary binary image via a moment-preserving thresholding operation;
wherein the $n^{th}$ primary binary image has a first $n^{th}$ plurality of particles comprising on-pixels;
(G) second translating the $n^{th}$ digital image into an $n^{th}$ alternate binary image via a predetermined thresholding operation;
wherein the $n^{th}$ alternate binary image has a second $n^{th}$ plurality of particles comprising on-pixels;
(H) filtering non-super-elevation particles from the $n^{th}$ alternate binary image, wherein the filtering comprises:
(i) removing from the $n^{th}$ alternate binary image all particles having a number of the on-pixels less than a threshold number of on-pixels, thereby creating an $n^{th}$ filtered binary image;
(I) multiplying the $n^{th}$ primary binary image with the $n^{th}$ filtered binary image, thereby creating an $n^{th}$ multiplied binary image;
wherein the $n^{th}$ multiplied binary image has a third $n^{th}$ plurality of particles comprising on-pixels;
(J) identifying the third $n^{th}$ plurality of particles as super-elevation particles associated with the selectively melting step (B);
(K) mapping the super-elevation particles, wherein the mapping comprises:
(i) determining a location of each of the super-elevation particles in the first multiplied binary image;
(ii) determining a size of each of the super-elevation particles in the $n^{th}$ multiplied binary image, wherein a total number of the on-pixels of the $n^{th}$ multiplied binary image comprising each of the super-elevation particles is representative of the size of its respective super-elevation particle;
(iii) mapping the location and size of each of the super-elevation particles to a respective location in the metal body;
(L) creating an $n^{th}$ layer of a three-dimensional volume quality model of the metal body based at least in part on the location and size of each of the super-elevation particles associated with the selectively melting step (B).

7. The method of claim 6, wherein the creating step comprises:
generating a two-dimensional contour of the $n^{th}$ metal layer of the metal body from a pre-designed three-dimensional model of the metal body;
integrating the location and size of each of the super-elevation particles into the two-dimensional contour of the $n^{th}$ metal layer, thereby producing an integrated contour; and
creating the $n^{th}$ layer of the three-dimensional volume quality model of the metal body based at least in part on the integrated contour of the $n^{th}$ metal layer.

8. The method of claim 6, wherein the predetermined thresholding operation of the second translating step (G) is a second predetermined thresholding operation, and wherein the first translating step (F) comprises performing a first predetermined thresholding operation on the -$n^{th}$ digital image.

9. The method of claim 6 wherein the moment-preserving thresholding operation of the first translating step (F) is a first moment-preserving thresholding operation, and wherein the second translating step (G) comprises performing a second moment-preserving thresholding operation on the $n^{th}$ digital image.

10. The method of claim 8, wherein the particles are $n^{th}$ particles, wherein the super-elevation particles are $n^{th}$ super-elevation particles, and wherein the method comprises:
selectively melting at least a portion of the $n^{th}$ layer of metal powder, thereby forming a melt pool comprising molten metal of the metal powder;
solidifying the molten metal into an $n^{th}$ layer of the metal body;
spreading an $n^{th}+2$ layer of metal powder on the $n^{th}+1$ metal layer;
obtaining an $n^{th}+1$ digital image of at least a portion of the $n^{th}+2$ layer of metal powder;
first translating the $n^{th}+1$ digital image into an $n^{th}+1$ primary binary image;
second translating the $n^{th}+1$ digital image into an $n^{th}+1$ alternate binary image;
filtering the $n^{th}+1$ alternate binary image, thereby creating a filtered $n^{th}+1$ alternate binary image;
multiplying the $n^{th}+1$ primary binary image with the filtered $n^{th}+1$ alternate binary image, thereby creating an $n^{th}+1$ multiplied binary image;
identifying all $n^{th}+1$ particles of the $n^{th}+1$ multiplied binary image as $n^{th}+1$ super-elevation particles associated with the selectively melting at least a portion of the $n^{th}+1$ layer of metal powder step;
mapping the $n^{th}+1$ super-elevation particles, thereby determining a location and size of each of the $n^{th}+1$ super-elevation particles;
creating $n^{th}+1$ layer of the three-dimensional volume quality model of the metal body based at least in part on the location and size of each of the $n^{th}+1$ super-elevation particles.

11. A method comprising:
(A) spreading a first layer of metal powder on a powder bed;
(B) selectively melting at least a portion of the first layer of metal powder, thereby forming a melt pool comprising molten metal of the metal powder;
(C) solidifying the molten metal into a first metal layer of a metal body;
(D) concomitant to the selectively melting step (B), obtaining a first sequential set of infrared images of the melt pool;
wherein each of the infrared images comprises a plurality of pixels;
wherein said each pixel of the plurality of pixels has a specific intensity value;
(E) correlating the specific intensity value of said each pixel of each of the infrared images of the first sequential set of infrared images to a peak temperature associated with the selectively melting step (B);
(F) mapping peak temperatures associated with the selectively melting step (B), wherein the mapping comprises:
(i) determining a peak temperature point in each of the infrared images of the first sequential set;
wherein each of the peak temperature points correspond to a pixel representing a highest temperature in each respective infrared image;
(ii) determining a location of each peak temperature points in its respective infrared image;
(iii) mapping the location of each of the peak temperature points in its respective infrared image to a location on the first metal layer, thereby creating a first digital temperature map of the first metal layer;
(G) creating a first layer of a three-dimensional volume quality model of the metal body based on the mapping step (F).

12. The method of claim 11, wherein the creating step comprises:
generating a two-dimensional contour of the first metal layer of the metal body from a pre-designed three-dimensional model of the metal body;
integrating the location and size of each of the peak temperature points into the two-dimensional contour of the first metal layer, thereby producing an integrated contour; and
creating the first layer of the three-dimensional volume quality model of the metal body based at least in part on the integrated contour of the first metal layer.

13. The method of claim 11 comprising:
spreading a second layer of metal powder on the first metal layer;
selectively melting at least a portion of the second layer of metal powder, thereby forming a melt pool comprising molten metal of the metal powder;
solidifying the molten metal into a second metal layer of the metal body;
concomitant to the selectively melting step, obtaining a second sequential set of infrared images of the melt pool;
correlating the specific intensity value of each pixel of each of the infrared images of the second sequential set to a peak temperature;
mapping the peak temperatures associated with the selectively melting at least a portion of the second layer step (B), wherein the mapping comprises:
creating a first layer of a three-dimensional volume quality model of the metal body based on the mapping step.

14. A method comprising:
(A) obtaining a first digital image with a camera, wherein the first digital image is of at least a portion of a powder bed including a layer of metal powder distributed over a layer of an additively manufactured body;
wherein the first digital image has a plurality of pixels;
wherein each pixel of the plurality of pixels has a specific intensity value;

(B) translating by a processor the first digital image into a first binary image having non-drag particles;
(C) filtering by the processor the non-drag particles from the first binary image:
(D) identifying by the processor all remaining particles in the first binary image as drag particles;
(E) preparing a map, wherein the preparing comprises mapping by the processor the drag particles, and wherein the mapping comprises mapping a series of coordinates of location, size, and type of each respective drag particle for the layer of the metal powder;
(F) registering the map in a list form;
(G) repeating (A)-(F) for a successive number of layers to create a defects registration list including the list for each of the successive number of layers, thereby producing a 3D CAD model of the additively manufactured body;
(H) converting by the processor the 3D CAD model to a plurality of 2D contours for each of the successive number of layers;
(I) extracting by the processor coordinates of detected defects from the defects registration list for a single layer and embedding the coordinates of the detected defects into a corresponding 2D contour for each of the successive number of layers;
(J) repeating (G) and (H) for each of the successive number of layers to yield a three-dimensional volume quality model of the additively manufactured body including all of the detected defects at each layer.

15. A method comprising:
(A) obtaining a first digital image of at least a portion of a powder bed including a layer of metal powder distributed over a layer of additively manufactured body; wherein the first digital image has a plurality of pixels; wherein each pixel of the plurality of pixels has a specific intensity value;
(B) translating the first digital image into a first binary image having non-drag particles;
(C) filtering the non-drag particles from the first binary image;
(D) identifying all remaining particles in the first binary image as drag particles
(E) preparing a map, wherein the preparing comprises mapping the drag particles and mapping a location and size of each respective drag particle;
(F) creating a first layer of a three-dimensional volume quality model of the additively manufactured body based at least in part on the location and size of each of the drag particles.

16. The method of claim 15, wherein the translating step comprises:
(i) determining a global average intensity value of the plurality of pixels;
(ii) resetting any specific intensity value that exceeds a threshold value to be equal to the global average intensity value;
(iii) determining a local average intensity value for said each pixel of the plurality of pixels;
(iv) subtracting the specific intensity value of each pixel of the plurality of pixels from the local average intensity value, thereby determining a background-corrected intensity value for each pixel of the plurality of pixels;
(v) replacing the specific intensity value of said each pixel with its determined background-corrected intensity value; and
(vi) performing a thresholding operation on the digital image, thereby creating the first binary image;

wherein the first binary image has a plurality of binary pixels; and
wherein the plurality of binary pixels comprises a plurality of particles.

17. The method of claim 15, wherein the filtering step comprises:
(i) performing an x-axis close operation on each binary pixel of the plurality of binary pixels;
(ii) removing from the first binary image all particles having a particle width below a threshold width;
(iii) removing from the first binary image all particles having a particle elongation ratio below a threshold ratio;
(iv) performing a dilation operation on the first binary image;
(v) determining the number of on-pixels in each row of the first binary image;
(vi) determining the number of particles in each row of the first binary image; and
(vii) switching any of the on-pixels to off-pixels for any of the pixels in a row of the first binary image where the row has either a number of on-pixels less than a threshold on-pixel number, or a number of particles greater than a threshold particle number.

18. The method of claim 15, wherein the preparing a map comprises:
(i) determining a location of each of the drag particles in the first binary image,
(ii) determining a size of each of the drag particles, wherein a total number of pixels comprising each drag particle is representative of the size of each respective drag particle; and
(iii) mapping the location and size of each of the drag particles, to a respective location in the powder bed.

19. A method comprising:
(A) utilizing a camera to obtain a first digital image of at least a portion of a powder bed including a layer of metal powder distributed over a layer of additively manufactured body and a portion of solidified molten metal indicative of an additively manufactured portion; wherein the first digital image has a plurality of pixels; wherein each pixel of the plurality of pixels has a specific intensity value;
(B) first translating with a processor the first digital image into a first primary binary image via a moment-preserving thresholding operation;
wherein the first primary binary image has a first plurality of particles comprising on-pixels;
(C) second translating with the processor the first digital image into a first alternate binary image via a predetermined thresholding operation;
wherein the first alternate binary image has a second plurality of particles comprising on-pixels;
(D) filtering with the processor at least some non-superelevation particles from the first alternate binary image, wherein the filtering comprises:
(i) removing from the first alternate binary image all particles having a number of the on-pixels less than a threshold number of on-pixels, thereby creating a first filtered binary image;
(E) multiplying the first primary binary image with the first filtered binary image, thereby creating a first multiplied binary image;
wherein the first multiplied binary image has a third plurality of particles comprising on-pixels;

(F) identifying the third plurality of particles as super-elevation particles associated with the additively manufactured portion in step (A);
(G) mapping the super-elevation particles, wherein the mapping comprises:
(i) determining a location of each of the super-elevation particles in the first multiplied binary image;
(ii) determining a size of each of the super-elevation particles in the first multiplied binary image, wherein a total number of the on-pixels of the first multiplied binary image comprising each of the super-elevation particles is representative of the size of its respective super-elevation particle;
(iii) mapping the location and size of each of the super-elevation particles to a respective location in the additively manufactured body; and
(H) creating a first layer of a three-dimensional volume quality model of the additively manufactured body based at least in part on the mapping step.

20. A method comprising:
(A) using a camera to obtain a first sequential set of infrared images of a melt pool, wherein the using the camera occurs concomitant to additively manufacturing of an additively manufactured body;
wherein each of the infrared images comprises a plurality of pixels;
wherein each pixel of the plurality of pixels has a specific intensity value;
(B) correlating the specific intensity value of each of the pixels of each infrared image of the first sequential set to a temperature;
(C) mapping the peak temperatures associated that from the using a camera step (A), wherein the mapping comprises:
(i) determining a peak temperature point in each of the infrared images of the first sequential set of infrared images;
wherein each of the peak temperature points corresponds to a pixel representing the highest temperature in each respective infrared image;
(ii) determining a location of each of the peak temperature points in its respective infrared image;
(iii) mapping the location of each of the peak temperature points in its respective infrared image to a location on a first metal layer of the additively manufactured body, thereby creating a first digital temperature map of the first metal layer;
(D) creating a first layer of a three-dimensional volume quality model of the additively manufactured body based on the mapping step (C).

* * * * *